United States Patent
Nagai

(10) Patent No.: US 10,463,329 B2
(45) Date of Patent: Nov. 5, 2019

(54) X-RAY DIAGNOSTIC APPARATUS AND X-RAY DIAGNOSTIC METHOD

(71) Applicant: TOSHIBA MEDICAL SYSTEMS CORPORATION, Otawara-Shi (JP)

(72) Inventor: Seiichirou Nagai, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 776 days.

(21) Appl. No.: 14/948,722

(22) Filed: Nov. 23, 2015

(65) Prior Publication Data

US 2016/0073988 A1 Mar. 17, 2016

Related U.S. Application Data

(63) Continuation of application No. PCT/JP2014/064022, filed on May 27, 2014.

(30) Foreign Application Priority Data

May 28, 2013 (JP) .................................. 2013-111977

(51) Int. Cl.
A61B 6/00 (2006.01)
A61B 6/03 (2006.01)

(52) U.S. Cl.
CPC .............. *A61B 6/481* (2013.01); *A61B 6/032* (2013.01); *A61B 6/4035* (2013.01);
(Continued)

(58) Field of Classification Search
CPC ..... A61B 6/032; A61B 6/4035; A61B 6/4042; A61B 6/42; A61B 6/4241; A61B 6/44;
(Continued)

(56) References Cited

U.S. PATENT DOCUMENTS 5,247,559 A * 9/1993 Ohtsuchi .................. H05G 1/26
378/53
5,285,489 A * 2/1994 Ohtsuchi .................. H05G 1/26
250/505.1
(Continued)

FOREIGN PATENT DOCUMENTS

JP 2000-69369 A 3/2000
JP 2001-8924 1/2001
(Continued)

OTHER PUBLICATIONS

A. Sarnelli et al., "K-edge digital subtraction imaging with dichromatic X-ray sources: SNR and dose studies," Physics in Medicine & Biology 51 (2006), 4311-4328.*
(Continued)

*Primary Examiner* — Allen C. Ho
(74) *Attorney, Agent, or Firm* — Oblon, McClelland, Maier & Neustadt, L.L.P.

(57) ABSTRACT

According to one embodiment, an X-ray diagnostic apparatus includes an X-ray tube, an X-ray detector and processing circuitry. The X-ray tube exposes an X-ray toward an object. The X-ray detector acquires two X-ray detection data sets by counting X-ray photons, having transmitted the object, in at least two X-ray energy bands depending on a K absorption edge of an X-ray absorber taken into the object. The processing circuitry is configured to input information to specify the X-ray absorber, set the at least two X-ray energy bands based on the input information to specify the X-ray absorber and generate at least one frame of X-ray image data by data processing including subtraction processing of the two X-ray detection data sets. The X-ray absorber has been depicted in the at least one frame of the X-ray image data.

10 Claims, 12 Drawing Sheets

(52) U.S. Cl.
CPC .............. *A61B 6/4042* (2013.01); *A61B 6/42* (2013.01); *A61B 6/4241* (2013.01); *A61B 6/44* (2013.01); *A61B 6/4429* (2013.01); *A61B 6/4435* (2013.01); *A61B 6/4441* (2013.01); *A61B 6/482* (2013.01); *A61B 6/504* (2013.01); *A61B 6/5205* (2013.01)

(58) Field of Classification Search
CPC ... A61B 6/4429; A61B 6/4435; A61B 6/4441; A61B 6/481; A61B 6/482; A61B 6/504
USPC ............ 378/5, 16, 19, 62, 98.8, 98.9, 98.11, 378/156–159, 196, 197; 250/370.09; 382/130
See application file for complete search history.

(56) References Cited

U.S. PATENT DOCUMENTS

| | | | | |
|---|---|---|---|---|
| 5,943,388 A * | 8/1999 | Tümer | ................. | G01V 5/0041 378/98.11 |
| 6,226,352 B1 * | 5/2001 | Salb | ................. | A61B 6/4035 378/143 |
| 6,246,747 B1 * | 6/2001 | Wear | ................. | G01N 23/083 378/98.11 |
| 6,563,906 B2 * | 5/2003 | Hussein | ................. | G01B 15/025 378/86 |
| 6,723,746 B2 * | 4/2004 | Salb | ................. | A61B 6/4035 424/9.4 |
| 6,751,290 B2 * | 6/2004 | Salb | ................. | A61B 6/4035 378/98.9 |
| 6,898,263 B2 * | 5/2005 | Avinash | ................. | A61B 6/032 378/4 |
| 6,950,492 B2 * | 9/2005 | Besson | ................. | A61B 6/032 378/16 |
| 6,999,549 B2 * | 2/2006 | Sabol | ................. | A61B 5/4872 378/5 |
| 7,466,793 B2 * | 12/2008 | Wu | ................. | A61B 6/032 378/19 |
| 7,649,981 B2 * | 1/2010 | Seppi | ................. | A61B 6/032 378/124 |
| 7,756,239 B2 * | 7/2010 | Wu | ................. | A61B 6/032 378/98.11 |
| 7,769,138 B2 * | 8/2010 | Dafni | ................. | A61B 6/4233 378/98.11 |
| 7,778,380 B2 * | 8/2010 | Altman | ................. | A61B 6/482 378/4 |
| 7,813,472 B2 * | 10/2010 | Proksa | ................. | A61B 6/032 378/19 |
| 7,852,978 B2 * | 12/2010 | Proksa | ................. | G01T 1/2985 378/19 |
| 7,869,862 B2 * | 1/2011 | Seppi | ................. | A61B 6/032 600/420 |
| 7,894,569 B2 * | 2/2011 | Proksa | ................. | A61B 6/032 378/5 |
| 7,920,674 B2 * | 4/2011 | Kang | ................. | A61B 6/4241 378/62 |
| 7,924,968 B2 * | 4/2011 | Proksa | ................. | G06T 11/006 378/4 |
| 8,000,440 B2 * | 8/2011 | Petch | ................. | A61B 6/4241 378/53 |
| 8,180,016 B2 | 5/2012 | Kanno | | |
| 8,213,566 B2 | 7/2012 | Roessl et al. | | |
| 8,218,837 B2 * | 7/2012 | Wu | ................. | A61B 6/032 382/128 |
| 8,311,182 B2 * | 11/2012 | Chandra | ................. | A61B 6/03 378/5 |
| 8,378,307 B2 * | 2/2013 | Baeumer | ................. | G01T 1/2985 250/362 |
| 8,422,636 B2 * | 4/2013 | Greenberg | ................. | G01T 7/005 378/207 |
| 8,442,184 B2 * | 5/2013 | Forthmann | ................. | A61B 6/032 378/5 |
| 8,592,773 B2 * | 11/2013 | Baeumer | ................. | G01T 1/17 250/370.09 |
| 8,611,489 B2 * | 12/2013 | Roessl | ................. | G01T 1/1647 378/5 |
| 8,615,120 B2 * | 12/2013 | Proksa | ................. | G06T 11/006 378/51 |
| 8,619,943 B2 * | 12/2013 | Flohr | ................. | A61B 6/032 378/19 |
| 8,625,740 B2 * | 1/2014 | Harding | ................. | G01N 23/20 378/207 |
| 8,653,471 B2 * | 2/2014 | Proksa | ................. | A61B 6/032 250/363.01 |
| 8,867,701 B2 * | 10/2014 | Kang | ................. | A61B 6/482 378/62 |
| 8,913,711 B2 * | 12/2014 | Moriyasu | ................. | A61B 6/03 378/4 |
| 9,014,455 B2 * | 4/2015 | Oh | ................. | A61B 6/52 378/98.11 |
| 9,044,189 B2 * | 6/2015 | Flohr | ................. | A61B 6/032 |
| 9,052,266 B2 * | 6/2015 | Miyazaki | ............. | A61B 6/4241 |
| 9,140,803 B2 * | 9/2015 | Bertram | ................. | A61B 6/032 |
| 9,165,349 B2 * | 10/2015 | Kwon | ................. | G06T 5/009 |
| 9,213,108 B2 * | 12/2015 | Nagai | ................. | A61B 6/4233 |
| 9,216,302 B2 * | 12/2015 | Kuwahara | ............. | A61N 5/1039 |
| 9,254,113 B2 * | 2/2016 | Kim | ................. | A61B 6/4241 |
| 9,269,168 B2 * | 2/2016 | Inglese | ................. | A61B 6/4241 |
| 9,274,235 B2 * | 3/2016 | Kang | ................. | G01N 23/04 |
| 9,330,440 B2 * | 5/2016 | Kwon | ................. | G06T 11/005 |
| 9,351,701 B2 * | 5/2016 | Yamakawa | ............ | A61B 6/025 |
| 9,354,331 B2 * | 5/2016 | Sagoh | ................. | A61B 6/032 |
| 9,360,439 B2 * | 6/2016 | Lu | ................. | A61B 6/4035 |
| 9,405,018 B2 * | 8/2016 | Proksa | ................. | G01N 23/046 |
| 9,414,797 B2 * | 8/2016 | Flohr | ................. | A61B 6/032 |
| 9,423,517 B2 * | 8/2016 | Kang | ................. | G01T 7/005 |
| 9,488,739 B2 * | 11/2016 | Pelc | ................. | G01T 1/247 |
| 9,492,132 B2 * | 11/2016 | Oh | ................. | A61B 6/482 |
| 9,492,133 B2 * | 11/2016 | Kang | ................. | A61B 6/405 |
| 9,533,173 B2 * | 1/2017 | Manzke | ................. | A61B 6/4241 |
| 9,595,101 B2 * | 3/2017 | Kato | ................. | G06T 11/005 |
| 9,678,220 B2 * | 6/2017 | Herrmann | ................. | G01T 1/17 |
| 9,693,742 B2 * | 7/2017 | Grasruck | ................. | A61B 6/06 |
| 9,730,759 B2 * | 8/2017 | Schirra | ................. | A61B 6/032 |
| 9,808,210 B2 * | 11/2017 | Yamazaki | ............. | A61B 6/032 |
| 9,861,324 B2 * | 1/2018 | Wang | ................. | A61B 6/482 |
| 9,925,278 B2 * | 3/2018 | Carmi | ................. | A61K 49/0414 |
| 9,928,585 B2 * | 3/2018 | Schirra | ................. | G06T 11/005 |
| 10,032,268 B2 * | 7/2018 | Carmi | ................. | A61B 6/481 |
| 2008/0137803 A1 | 6/2008 | Wu et al. | | |
| 2008/0167552 A1 | 7/2008 | Bouchevreau et al. | | |
| 2011/0096905 A1 | 4/2011 | Roessl et al. | | |

FOREIGN PATENT DOCUMENTS

| | | |
|---|---|---|
| JP | 2003-38475 | 2/2003 |
| JP | 2004-8460 | 1/2004 |
| JP | 2004-508124 A | 3/2004 |
| JP | 2004-325183 | 11/2004 |
| JP | 2008-161690 A | 7/2008 |
| JP | 2011-527223 | 10/2011 |
| JP | 2013-57554 A | 3/2013 |
| WO | WO 02/22018 A2 | 3/2002 |
| WO | WO 2009/022625 A1 | 2/2009 |

OTHER PUBLICATIONS

A. Sarnelli et al., "K-edge digital subtraction imaging based on a dichromatic and compact X-ray source," Physics in Medicine & Biology 49 (2004), 3291-3305.*

International Preliminary Report on Patentability and Written Opinion dated Dec. 10, 2015 in PCT/JP2014/064022 (English Translation only).

Office Action dated Nov. 22, 2016 in Japanese Patent Application No. 2013-111977 (with unedited computer generated English language translation).

International Search Report dated Jul. 1, 2014 in PCT/JP2014/064022, filed on May 27, 2014 ( with English Translation).

(56) References Cited

OTHER PUBLICATIONS

Written Opinion dated Jul. 1, 2014 in PCT/JP2014/064022, filed on May 27, 2014.
Office Action dated Jun. 27, 2017 in Japanese Patent Application No. 2013-111977.

* cited by examiner

| SUBSTANCE | TUBE VOLTAGE | BEAM FILTER | $W_1$ | $W_2$ |
|---|---|---|---|---|
| IODINE(I) | 50 | Al | a1 | b1 |
| | 60 | Al | a2 | b2 |
| | ... | ... | ... | ... |
| | 120 | Al | ax | bx |
| | 50 | Ta | c1 | d1 |
| | ... | ... | ... | ... |
| | 120 | Ta | cx | dx |
| GOLD(Au) | 50 | Al | e1 | f1 |
| | ... | ... | ... | ... |
| | 120 | Al | ex | fx |
| ... | ... | ... | ... | ... |

FIG. 10

| IMAGING PURPOSE | SUBSTANCE | TUBE VOLTAGE | BEAM FILTER | W₁ | W₂ | TH1 | TH2 | TH3 |
|---|---|---|---|---|---|---|---|---|
| USUAL X-RAY IMAGING | | 50 | Al | p1 | q1 | p11 | q21 | pq31 |
| | | 60 | Al | p2 | q2 | p12 | q22 | pq32 |
| | | ⋮ | ⋮ | ⋮ | ⋮ | ⋮ | ⋮ | ⋮ |
| | | 120 | Al | px | qx | p1x | q2x | pq3x |
| K ABSORPTION EDGE SUBTRACTION METHOD | IODINE(I) | 50 | Ta | r1 | s1 | r11 | s21 | rs31 |
| | | ⋮ | ⋮ | ⋮ | ⋮ | ⋮ | ⋮ | ⋮ |
| | | 120 | Ta | rx | sx | r1x | s2x | rs3x |
| | | 50 | Al | a1 | b1 | a11 | b21 | ab31 |
| | | 60 | Al | a2 | b2 | a12 | b22 | ab32 |
| | | ⋮ | ⋮ | ⋮ | ⋮ | ⋮ | ⋮ | ⋮ |
| | | 120 | Al | ax | bx | a1x | b2x | ab3x |
| | GOLD(Au) | 50 | Ta | c1 | d1 | c11 | d21 | cd31 |
| | | 120 | Ta | cx | dx | c1x | d2x | cd3x |
| | | 50 | Al | e1 | f1 | e11 | f21 | ef31 |
| | | ⋮ | ⋮ | ⋮ | ⋮ | ⋮ | ⋮ | ⋮ |
| | | 120 | Al | ex | fx | e1x | f2x | ef3x |
| | ⋮ | ⋮ | | | | | | ⋮ |

FIG. 17

X-RAY DIAGNOSTIC APPARATUS AND X-RAY DIAGNOSTIC METHOD

CROSS REFERENCES TO RELATED APPLICATIONS

This is a continuation of Application PCT/JP2014/64022, filed on May 27, 2014.

This application is based upon and claims the benefit of priority from Japanese Patent Application No. 2013-111977 filed on May 28, 2013; the entire contents of which are incorporated herein by reference.

FIELD

Embodiments described herein relate generally to an X-ray diagnostic apparatus and an X-ray diagnostic method.

BACKGROUND

As a diagnostic method by an X-ray diagnostic apparatus, the K absorption edge subtraction method has been devised. The K absorption edge is a discontinuous point in the energy direction of X-ray photons which exist in an X-ray absorption characteristic of a substance. The energy at the K absorption edge of iodine used as a contrast agent is about 33.169 keV.

In the conventional K absorption edge subtraction method, an X-ray which has an energy slightly lower than the energy at a K absorption edge and an X-ray which has an energy slightly higher than the energy at the K absorption edge are emitted at a short time interval, using an X-ray source which generates highly monochromatic X-rays. Then, subtraction processing of two frames of X-ray image data acquired by exposing X-rays which have different energies is performed.

When an interval of imaging by exposing X-rays which have two energies is sufficiently short, compared to a moving speed of a human body, the human body can be considered as static. While the X-ray absorption characteristic of iodine is significantly different between energies lower and higher than the K absorption edge, the X-ray absorption characteristics of substances constituting a human body are approximately equal. Accordingly, the K absorption edge subtraction method allows removing the structure of a human body from image data.

PRIOR TECHNICAL LITERATURE

[Patent literature 1] JPA 2004-8460
[Patent literature 2] JPA 2004-325183

However, the conventional K absorption edge subtraction method requires a special X-ray source with high monochromaticity. In general, although a synchrotron radiation X-ray source is necessary, the synchrotron radiation X-ray source cannot be used in general hospitals.

Furthermore, the conventional K absorption edge subtraction method has a problem that the structure of a human body remains in subtraction image data when the human body moves to a non-negligible extent between exposures of X-rays having different energies.

Thus, an object of the present invention is to provide an X-ray diagnostic apparatus and an X-ray diagnostic method which can acquire X-ray image data, where the structure of a human body has been removed enough and an interested substance, such as a contrast agent, has been depicted more clearly, using a practical configuration by taking advantage of the K absorption edge of the interested substance.

BRIEF DESCRIPTION OF THE DRAWINGS

In the accompanying drawings:

FIG. 10 shows an example of table to be stored in the threshold storage part shown in FIG. 3;

FIG. 17 shows an example of table showing threshold voltages to be stored in the threshold storage part shown in FIG. 3.

DETAILED DESCRIPTION

In general, according to one embodiment, an X-ray diagnostic apparatus includes an X-ray tube, an X-ray detector and processing circuitry. The X-ray tube exposes an X-ray toward an object. The X-ray detector acquires two X-ray detection data sets by counting X-ray photons, having transmitted the object, in at least two X-ray energy bands depending on a K absorption edge of an X-ray absorber taken into the object. The processing circuitry is configured to input information to specify the X-ray absorber, set the at least two X-ray energy bands based on the input information to specify the X-ray absorber and generate at least one frame of X-ray image data by data processing including subtraction processing of the two X-ray detection data sets. The X-ray absorber has been depicted in the at least one frame of the X-ray image data.

Further, according to one embodiment, an X-ray diagnostic method includes: inputting information to specify an X-ray absorber taken into an object; setting at least two X-ray energy bands, depending on a K absorption edge of the X-ray absorber, based on the input information to specify the X-ray absorber; exposing an X-ray toward the object; acquiring two X-ray detection data sets by counting X-ray photons, having transmitted the object, in the at least two X-ray energy bands; and generating at least one frame of X-ray image data by data processing including subtraction processing of the two X-ray detection data sets. The X-ray absorber is depicted in the at least one frame of the X-ray image data.

An X-ray diagnostic apparatus and an X-ray diagnostic method according to embodiments of the present invention will be described with reference to the accompanying drawings.

(Configuration and Function)

Figure 1:
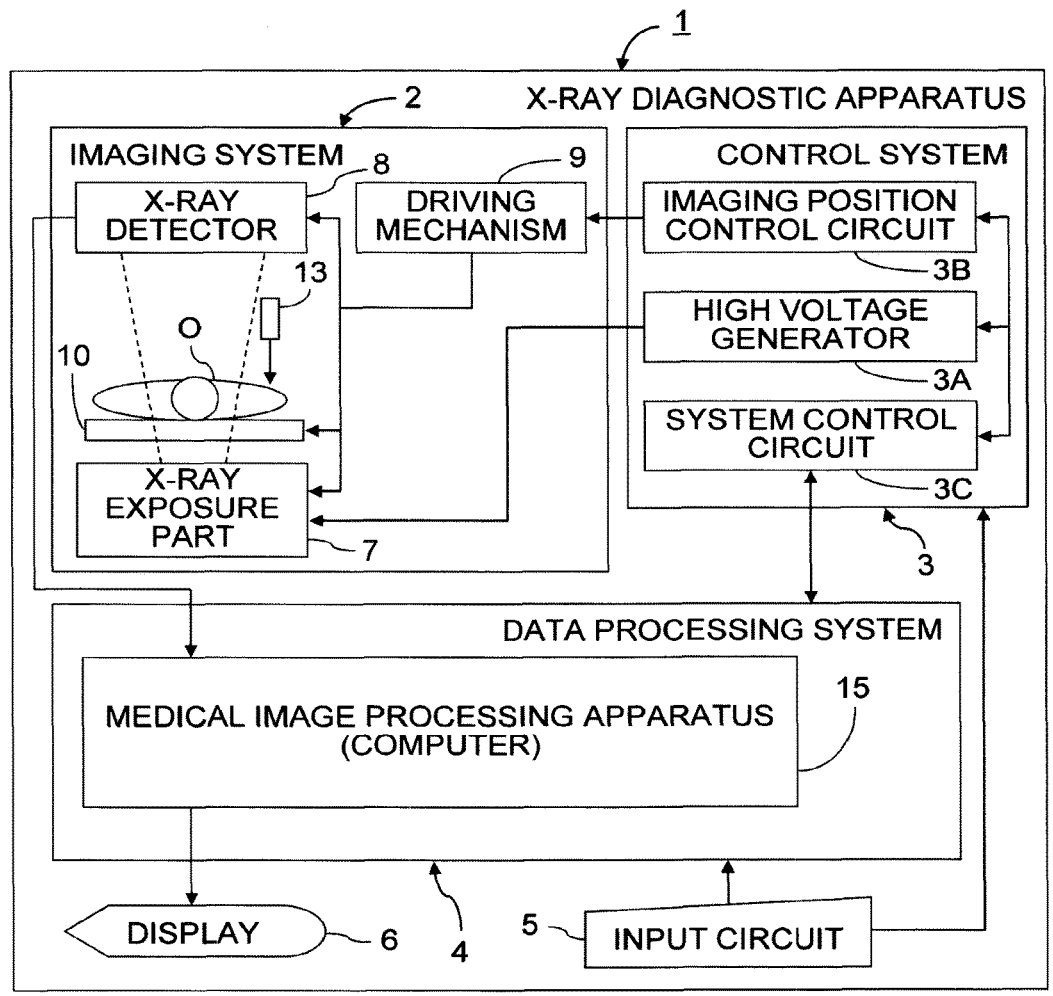
FIG. 1 is a configuration diagram of an X-ray diagnostic apparatus according to an embodiment of the present invention.

FIG. 1 is a configuration diagram of an X-ray diagnostic apparatus according to an embodiment of the present invention.

An X-ray diagnostic apparatus 1 includes an imaging system 2, a control system 3, a data processing system 4, an input circuit 5, and a display 6. The imaging system 2 has an X-ray exposure part 7, an X-ray detector 8, a driving mechanism 9, and a bed 10. The control system 3 has a high voltage generator 3A, an imaging position control circuit 3B, and a system control circuit 3C.

The X-ray exposure part 7 includes an X-ray tube and a beam filter. The X-ray exposure part 7 is disposed opposite to the X-ray detector 8 so that the X-ray exposure part 7 and the X-ray detector 8 lie at both sides of an interjacent object O set on the bed 10. The X-ray exposure part 7 and the X-ray detector 8 can change their angles and relative positions to the object O, with keeping a relative position between the X-ray exposure part 7 and the X-ray detector 8, by driving of the driving mechanism Specifically, the X-ray exposure part 7 and the X-ray detector 8 are fixed to both ends of a C-shaped arm which has a rotation function. The X-ray exposure part 7 is configured to expose an X-ray from a predetermined angle toward the object O with the X-ray tube so that the X-ray which has transmitted the object O can be detected by the X-ray detector 8.

The driving mechanism 9 can adjust an inclination and a position of a top plate of the bed 10. Furthermore, a contrast agent injector 13 for injecting a contrast agent into the object O set on the bed 10 is installed near the object O.

FIG. 1 shows an example of the X-ray diagnostic apparatus 1 for circulatory organs. The X-ray exposure part 7, the X-ray detector 8, and the bed 10 may be disposed differently depending on an intended purpose, such as for breast imaging.

The high voltage generator 3A of the control system 3 applies a high voltage to the X-ray tube of the X-ray exposure part 7 to expose an X-ray having a desired energy toward the object O. The imaging position control circuit 3B outputs control signals to the driving mechanism 9 to control the driving mechanism 9. Specifically, a rotation angle and a position of the X-ray exposure part 7 and the X-ray detector 8, and an inclination and a position of the top plate of the bed 10 are controlled by control signals which are output to the driving mechanism 9 from the imaging position control circuit 3B.

The system control circuit 3C controls elements of the X-ray diagnostic apparatus 1, including the high voltage generator 3A, the imaging position control circuit 3B, and the data processing system 4.

The data processing system 4 generates X-ray image data showing characteristic information of the object O, based on X-ray detection data detected by the X-ray detector 8. The data processing system 4 can be configured by a computer 15. The computer 15 functions as a medical image processing apparatus 15 by executing a medical image processing program. That is, the medical image processing apparatus 15 is built in the X-ray diagnostic apparatus 1.

Note that, an independent medical image processing apparatus having similar functions may also be coupled to the X-ray diagnostic apparatus 1 through a network. In that case, the independent medical image processing apparatus has a function as a data obtaining part which is configured to obtain X-ray detection data from the X-ray diagnostic apparatus 1 through the network. As described above, the medical image processing apparatus 15 built in the X-ray diagnostic apparatus 1 or a medical image processing apparatus coupled to the X-ray diagnostic apparatus 1 through a network can be configured by processing circuitry, such as a computer.

Next, configurations and functions of the X-ray detector 8 will be described.

Figure 2:
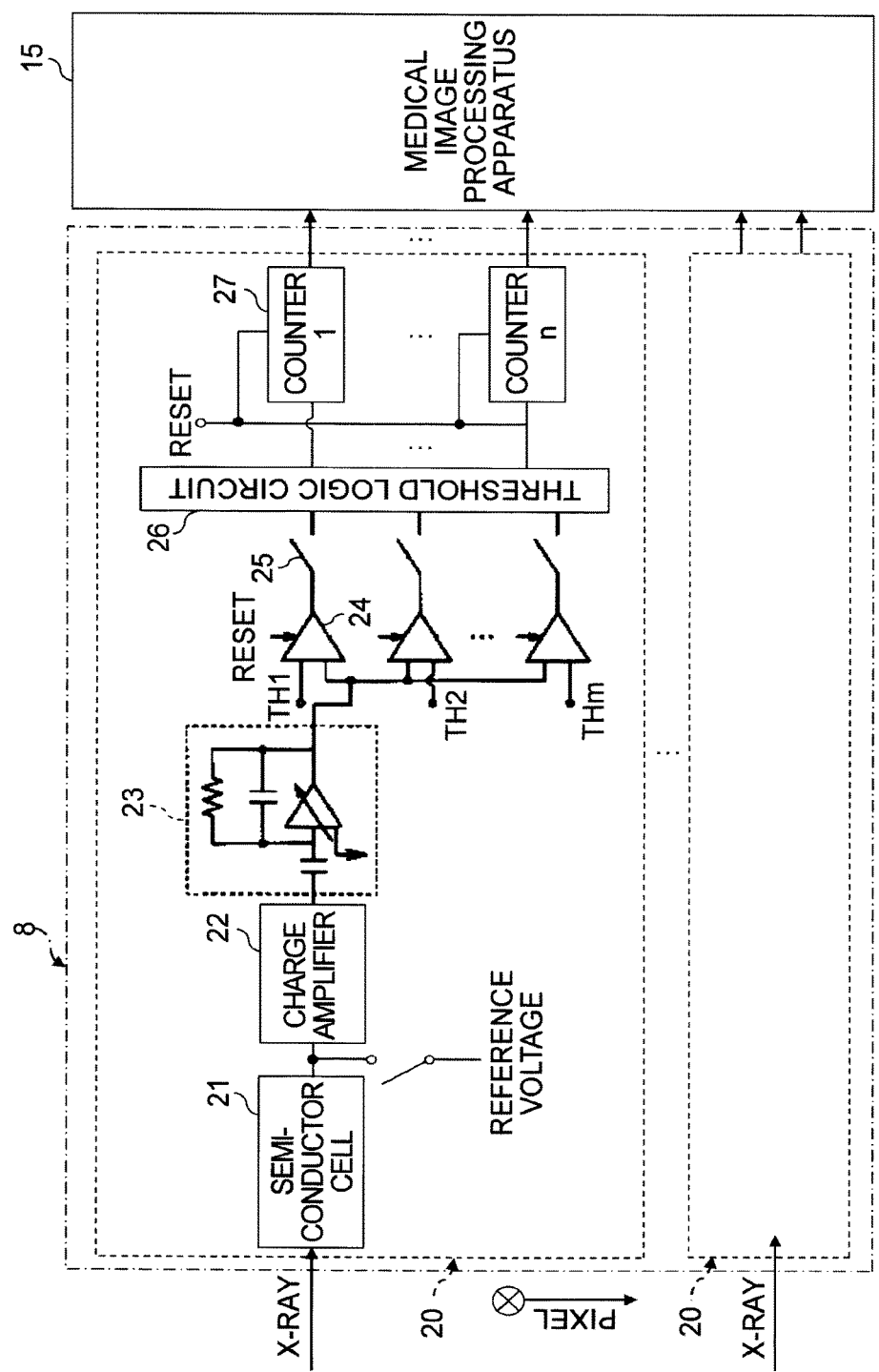
FIG. 2 shows an example of detailed structure of the X-ray detector shown in FIG. 1.

FIG. 2 shows an example of detailed structure of the X-ray detector 8 shown in FIG. 1.

The X-ray detector 8 is composed using photon counting type image sensors 20 arrayed two-dimensionally. Each of the image sensors 20 corresponds to a pixel. Therefore, the same number of the image sensors 20 as the number of pixels are arranged.

Therefore, when pixels of the X-ray detector 8 are one dimension, the X-ray detector 8 can be configured by arraying the image sensors 20 in one dimension. Note that, an example case where the X-ray detector 8 has practical two dimensional pixels will be described here.

Each of the image sensors 20 has a function to detect incident X-ray photons and count the X-ray photons for every energy level. Therefore, each of the image sensors 20 discriminates energies of incident X-ray photons. Specifically, each of the image sensors 20 generates an electric pulse depending on an energy of an incident X-ray photon, classifies pulse heights of the generated electric pulses into levels, and performs processing of counting the classified electric pulses for every level. Note that, noises can be reduced by not counting each electric pulse whose wave height value is smaller than a predetermined threshold.

In the example shown in FIG. 2, each of the image sensors 20 is composed of a semiconductor cell 21, a charge amplifier 22, a waveform shaping circuit 23, comparators 24, switches 25, a threshold logic circuit 26, and counters 27, in order to have the functions as described above.

The semiconductor cell 21 can be configured by a cadmium telluride (CdTe) semiconductor, a cadmium zinc telluride (CdZnTe) semiconductor, a silicon (Si) semiconductor or the like. The output side of the semiconductor cell 21 is coupled to the charge amplifier 22.

The charge amplifier 22 charges up an electric charge collected in response to an X-ray photon incident on the semiconductor cell 21, and outputs the charged up electric charge as a pulse signal having an electric quantity. The output side of the charge amplifier 22 is coupled to the waveform shaping circuit 23.

The waveform shaping circuit 23 adjusts frequency characteristic of each pulse signal output from the charge amplifier 22, and shapes a waveform of each pulse signal by giving a gain and an offset. A gain and an offset for waveform shaping are adjusted so that non-uniformity in inherent characteristics of the semiconductor cell 21 and the charge amplifier 22 is reduced. Thereby, a pulse signal output from the waveform shaping circuit 23 has a characteristic corresponding to an amount of energy of an X-ray photon incident on the semiconductor cell 21.

The output side of the waveform shaping circuit 23 is coupled to the m pieces of comparators 24 which are coupled to each other in parallel. The switch 25 is connected with the subsequent part of each of the m comparators 24. Thus, a pulse signal output from the waveform shaping circuit 23 passes through either one of the comparators 24, depending on the corresponding amount of energy of X-ray photon. Then, the pulse signal switches the switch 25, coupled to the comparator 24 through which the pulse signal has passed, to ON.

Specifically, threshold voltages TH1, TH2, TH3, ..., THm, which are different from each other, are applied to reference input terminals of the comparators 24 respectively. That is, an amplitude of a pulse signal which is input to each of the comparators 24 is compared with each of the threshold voltages TH1, TH2, TH3, ..., THm. As a result, only a pulse signal exceeding one of the threshold voltages TH1, TH2, TH3, ..., THm, is output from the corresponding comparator 24, and switches the switch 25 coupled to the corresponding comparator 24 to ON. Note that, pulse signals each having an amplitude not more than the smallest threshold voltage TH1 are considered as noises and removed.

The input side of the threshold logic circuit 26 is coupled to the switches 25. Meanwhile, the output side of the threshold logic circuit 26 is coupled to the counters 27, corresponding to energy bands of X-ray photons to be discriminated, which are in parallel. The threshold logic circuit 26 measures between which threshold voltages TH1, TH2, TH3, ..., THm an amplitude of a pulse signal is, by determining whether each of the switches 25 has been switched to the ON state. Each measurement result of an amplitude of a pulse signal in the threshold logic circuit 26 is output as an energy discrimination signal to the corresponding one of the counters 27.

Thereby, the counters 27 can count the number of X-ray photons incident on the semiconductor cell 21 for every energy band. The respective counters 27 output number counting results of X-ray photons as digital data. Therefore, each image sensor 20 corresponding to one pixel of the X-ray detector 8 outputs number counting results, corresponding to energy bands, as X-ray detection data.

When the number of energy bands of X-ray photons to be discriminated and the counters 27 in each of the image sensors 20 of the X-ray detector 8 are n, a number counting signal $C(xp, E_i)$ which is output from the i-th counter 27 as a number counting result is expressed by expression (1).

$$C(xp,E_i)=\int_i dE \cdot \varphi(E) \cdot Matt(E) \cdot Patt(E,xp) \cdot Dabs(E,xd) \quad (1)$$

wherein
xp: a thickness of substances constituting the object O on a path of an X-ray,
E: an energy of an X-ray photon,
$E_i$: the central energy of the i-th energy band to be discriminated in the image sensor 20,
$\int_i dE$: an integration from $(E_i-\Delta E/2)$ to $(E_i+\Delta E/2)$,
$\Delta E$: a width of an energy band to be discriminated in the image sensor 20, $\varphi(E)$: an energy density of an X-ray photon, having the energy E, which has been emitted from the X-ray tube toward a corresponding pixel and transmitted a beam filter,
Matt(E): an absorption characteristic, to an X-ray having the energy E, by X-ray absorbers which exist between the X-ray tube and a detection plane of the X-ray detector 8,
Patt(E, xp): an absorption characteristic, to an X-ray having the energy E, by the object O,
Dabs(E, xd): an absorption characteristic, to an X-ray having the energy E, by the X-ray detector 8, and
xd: a thickness of substances constituting the X-ray detector 8.

Examples of an X-ray absorber include a top plate, a bucky cover, an X-ray transmission part of a grid, a cover on an incident part of the X-ray detector 8, and a press plate used for a breast imaging apparatus.

Since the function in the integration in expression (1) is continuous, there is an energy $E_i'$ $(E_i-\Delta E/2 < E_i' < E_i+\Delta E/2)$ which has expression (2) to be satisfied.

$$C(xp,E_i)=\varphi(E_i') \cdot Matt(E_i') \cdot Patt(E_i',xp) \cdot Dabs(E_i',xd) \cdot \Delta E \quad (2)$$

In expression (2), $\varphi(E_i') \cdot \Delta E$ corresponds to the number of X-ray photons in the i-th energy band. Thus, when $\varphi(E_i') \cdot \Delta E$ is represented as N(i), the number counting signal $C(xp, E_i)$ which is output from the counter 27 is expressed by expression (3).

$$C(xp,E_i)=N(i) \cdot Matt(E_i') \cdot Patt(E_i',p) \cdot Dabs(E_i',xd) \quad (3)$$

wherein
N(i): the number of X-ray photons in the i-th energy band, out of X-ray photons emitted from the X-ray tube toward a corresponding pixel.

Similarly, when a contrast agent is included in the object O, the number counting signal $C(xp, xc, E_i)$, which is output as a number counting result of X-ray photons in the i-th energy band, is expressed by expression (4).

$$C(xp,xc,E_i)=N(i) \cdot Matt(E_i') \cdot Patt(E_i',xp) \cdot Catt(E_i',xc) \cdot Dabs(E_i',xd) \quad (4)$$

wherein
xp: a thickness of substances constituting the object O on a path of an X-ray,
xc: a thickness of a substance constituting the contrast agent on a path of an X-ray,
$E_i$: the central energy of the i-th energy band to be discriminated in the image sensor 20,
$\Delta E$: a width of an energy band to be discriminated in the image sensor 20,
N(i): the number of X-ray photons in the i-th energy band, out of X-ray photons emitted from the X-ray tube toward a corresponding pixel,
Matt($E_i'$): an absorption characteristic of X-ray corresponding to the energy $E_i'$ by X-ray absorbers which exist between the X-ray tube and the detection plane of the X-ray detector 8,
Patt($E_i'$, xp): an absorption characteristic of X-ray corresponding to the energy $E_i'$ by the object O,
Catt($E_i'$, xc): an absorption characteristic of X-ray corresponding to the energy $E_i'$ by the contrast agent,
Dabs($E_i'$, xd): an absorption characteristic of X-ray corresponding to the energy $E_i'$ by the X-ray detector 8, and
xd: a thickness of substances constituting the X-ray detector 8.

Examples of a contrast agent include iodine, barium, and gadolinium. A drug containing a heavy metal or a device inserted into a blood vessel can also be treated in calculation similarly to a contrast agent. Examples of a device include a catheter, a guide wire, and a stent.

The X-ray absorption characteristic Patt($E_i'$, xp) by the object O, the X-ray absorption characteristic Catt($E_i'$, xc) by a contrast agent, and the X-ray absorption characteristic Dabs($E_i'$, xd) by the X-ray detector 8, which are included as parameters in the above-mentioned expressions, are expressed by expression (5), expression (6), and expression (7), respectively.

$$Patt(Ei',xp)=\exp\{-\mu p(E_i')\cdot xp\} \quad (5)$$

$$Catt(E_i',xc)=\exp\{-\mu c(E_i')\cdot xc\} \quad (6)$$

$$Dabs(E_i',xd)=1-\exp\{-\mu d(E_i')\cdot xd\} \quad (7)$$

wherein $\mu p(E_i')$: an X-ray absorption coefficient, corresponding to the energy $E_i'$, of substances constituting the object O, $\mu c(E_i')$: an X-ray absorption coefficient, corresponding to the energy $E_i'$, of substances constituting a contrast agent, and $\mu d(E_i')$: an X-ray absorption coefficient, corresponding to the energy $E_i'$, of substances constituting the X-ray detector 8.

The substances constituting the object O include hydrogen H, carbon C, oxygen O, and nitrogen N. That is, the object O strictly consists of a plurality of substances. However, X-ray image data are generated without distinguishing the substances constituting the object O in the conventional X-ray diagnostic apparatus. Therefore, the substances constituting the object O are treated as one typical element or one virtual average element here, from a viewpoint of generating X-ray image data which have characteristics similar to those of X-ray image data acquired by the conventional X-ray diagnostic apparatus. Since a material constituting a detection layer of the X-ray detector 8 is not changed in many cases, the material of the detection layer is not shown as a function argument.

Next, functions of the medical image processing apparatus 15 will be described.

Figure 3:
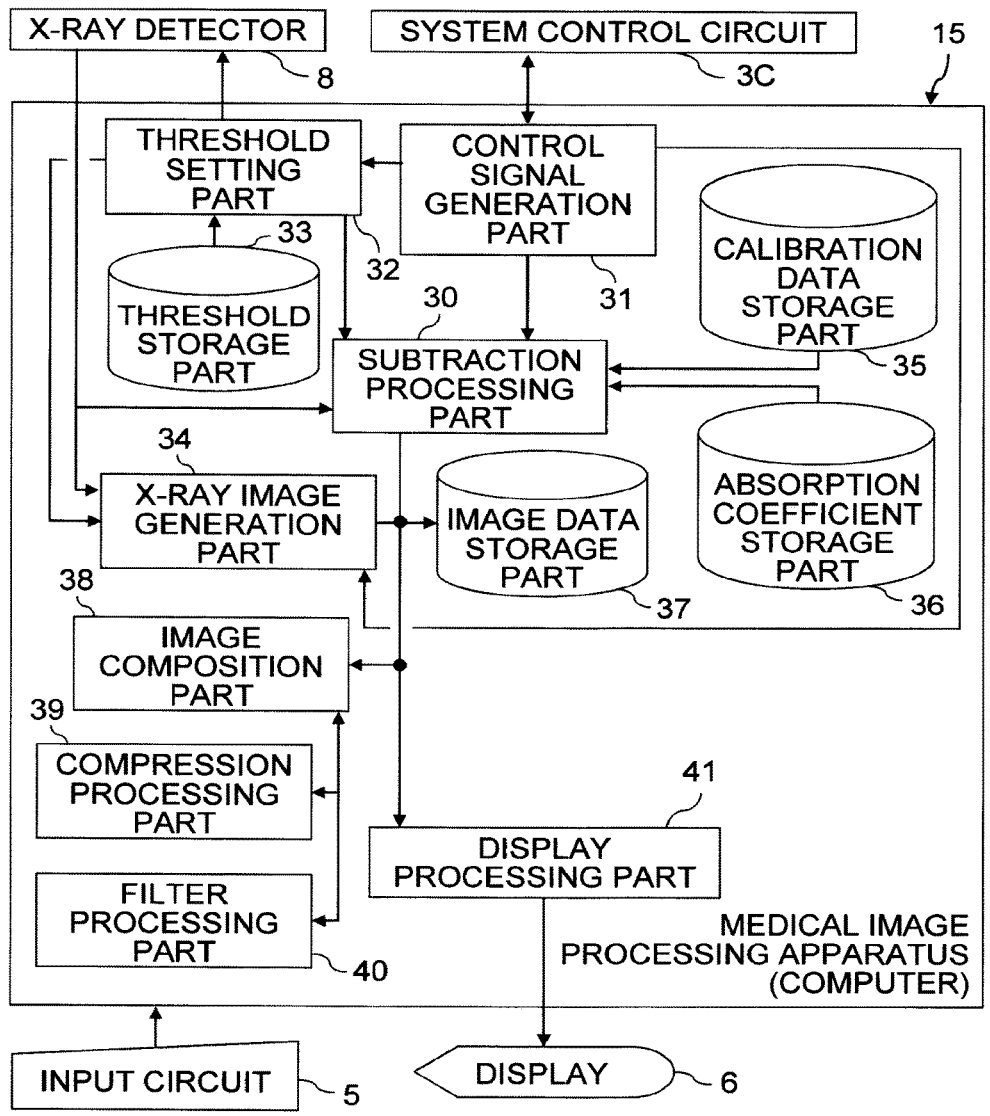
FIG. 3 is a detailed configuration diagram of the medical image processing apparatus shown in FIG. 1.

FIG. 3 is a detailed configuration diagram of the medical image processing apparatus 15 shown in FIG. 1.

The medical image processing apparatus 15 has a subtraction processing part 30, a control signal generation part 31, a threshold setting part 32, a threshold storage part 33, an X-ray image generation part 34, a calibration data storage part 35, an absorption coefficient storage part 36, an image data storage part 37, an image composition part 38, a compression processing part 39, a filter processing part 40, and a display processing part 41.

Note that, elements having functions to store information, such as the threshold storage part 33, the calibration data storage part 35, the absorption coefficient storage part 36, and the image data storage part 37, can be configured by at least one storage circuit included in the processing circuitry which configures the medical image processing apparatus 15. Alternatively, the elements having functions to store information, such as the threshold storage part 33, the calibration data storage part 35, the absorption coefficient storage part 36, and the image data storage part 37, may also be configured by at least one storage circuit which has been installed separately from the processing circuitry configuring the medical image processing apparatus 15. Furthermore, the processing circuitry configuring the medical image processing apparatus 15 may also be integrated with circuitry configuring the system control circuit 3C, the imaging position control circuit 3B and/or the like of the control system 3.

The control signal generation part 31 has a function to control the X-ray exposure part 7 and the driving mechanism 9 through the high voltage generator 3A and the imaging position control circuit 3B by outputting control signals depending on examination information to the system control circuit 3C of the control system 3.

The threshold setting part 32 has a function to set threshold values for discriminating energies of X-ray photons in each of the image sensors 20 of the X-ray detector 8, and apply the threshold voltages TH1, TH2, TH3, . . . , THm corresponding to the set threshold values to the comparators 24 respectively. That is, energy bands for discriminating X-ray photons can be determined by setting the threshold voltages TH1, TH2, TH3, . . . , THm in the threshold setting part 32.

Figure 4:
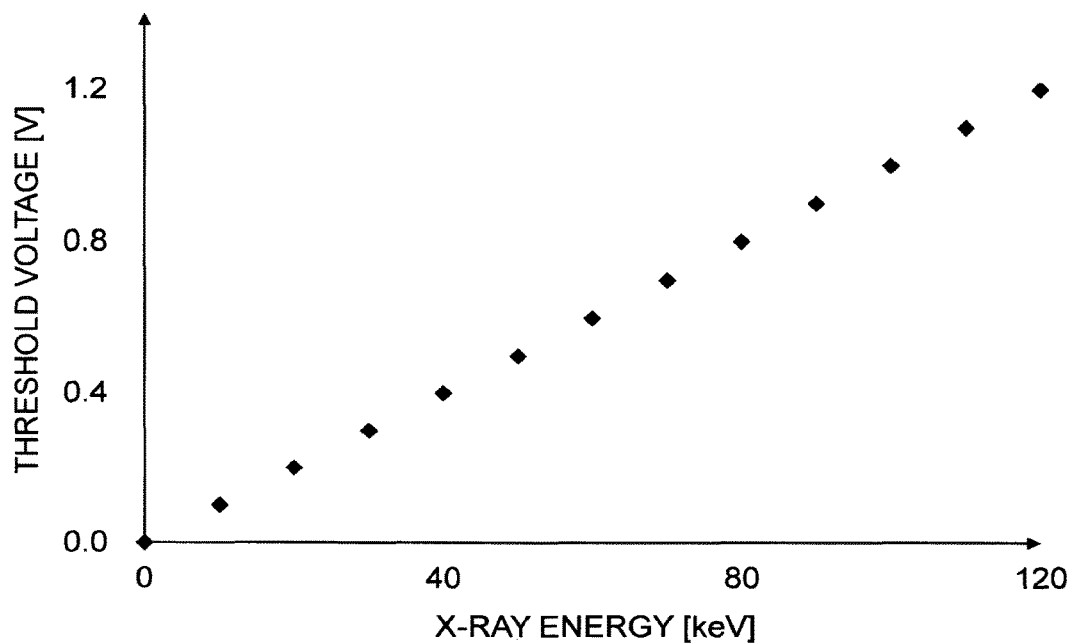
FIG. 4 shows an example of relationship between discriminated energies of X-ray photons and threshold voltages set in the threshold setting part shown in FIG. 3.

FIG. 4 shows an example of relationship between discriminated energies of X-ray photons and threshold voltages set in the threshold setting part 32 shown in FIG. 3.

In FIG. 4, the horizontal axis shows energies [keV] of X-ray photons incident on each image sensor 20 of the X-ray detector 8 while the vertical axis shows threshold voltages [V] applied to the comparators 24 of each image sensor 20. As shown in FIG. 4, boundaries of energy bands can be variably set by adjusting threshold voltages applied to the comparators 24.

In particular, the threshold setting part 32 is configured to determine two energy bands near a K absorption edge by adjusting threshold voltages so that subtraction image data can be generated by the K absorption edge subtraction method. That is, the threshold setting part 32 has a function as an energy band setting part which is configured to set two X-ray energy bands depending on a K absorption edge of an X-ray absorber of interest injected or inserted into the object O. Therefore, in the case of X-ray imaging by the K absorption edge subtraction method, the X-ray detector 8 acquires two X-ray detection data sets by counting X-ray photons transmitted the object O in two energy bands at each of pixel positions.

Figure 5:
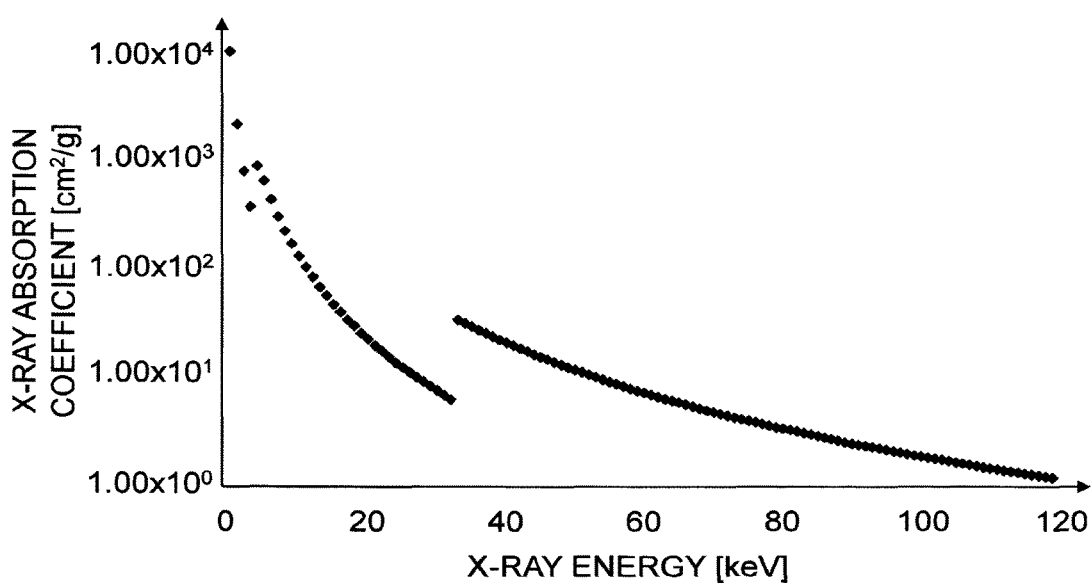
FIG. 5 shows the X-ray absorption characteristic of iodine used as a contrast agent in X-ray imaging by the X-ray diagnostic apparatus shown in FIG. 1.

FIG. 5 shows the X-ray absorption characteristic of iodine used as a contrast agent in X-ray imaging by the X-ray diagnostic apparatus 1 shown in FIG. 1.

In FIG. 5, the horizontal axis shows energies [key] of X-ray photons while the vertical axis shows absorption coefficients [$cm^2/g$] of X-ray photons by iodine. As shown in FIG. 5, the absorption coefficients of X-ray photons by iodine becomes discontinuous in the energy direction of X-ray photons. The energy at the discontinuous point of the absorption coefficients of X-ray photons is called K absorption edge. The energy at the K absorption edge of iodine used as a contrast agent is 33.1694 keV.

As a contrast agent, xenon whose energy at the K absorption edge is 34.5614 keV, barium whose energy at the K absorption edge is 37.4406 keV, and gadolinium whose energy at the K absorption edge is 50.2391 keV are typical besides iodine. Furthermore, gold whose energy at the K absorption edge is 80.7249 keV is generally used as a medicine or a mark on the tip of a guide wire, which can be treated similarly to a contrast agent.

In order to generate subtraction image data by the K absorption edge subtraction method, it is necessary to count the number of X-ray photons each having an energy higher than the energy at the K absorption edge of a contrast agent exemplified in FIG. 5 and the number of X-ray photons each having an energy lower than the energy at the K absorption edge of the contrast agent, respectively, to perform subtraction processing thereof.

Therefore, it is important to set divided n energy bands so that the i-th energy band out of the n energy bands becomes lower than an energy Ek at the K absorption edge of a contrast agent while the (i+1)-th energy band becomes higher than the energy Ek at the K absorption edge of the contrast agent. However, the boundary between the i-th energy band and the (i+1)-th energy band has no relation with the energy Ek at the K absorption edge of the contrast agent. Therefore, when energy bands are set arbitrarily, the energy Ek at the K absorption edge of the contrast agent is to be included in the i-th or the (i+1)-th energy band.

Figure 6:
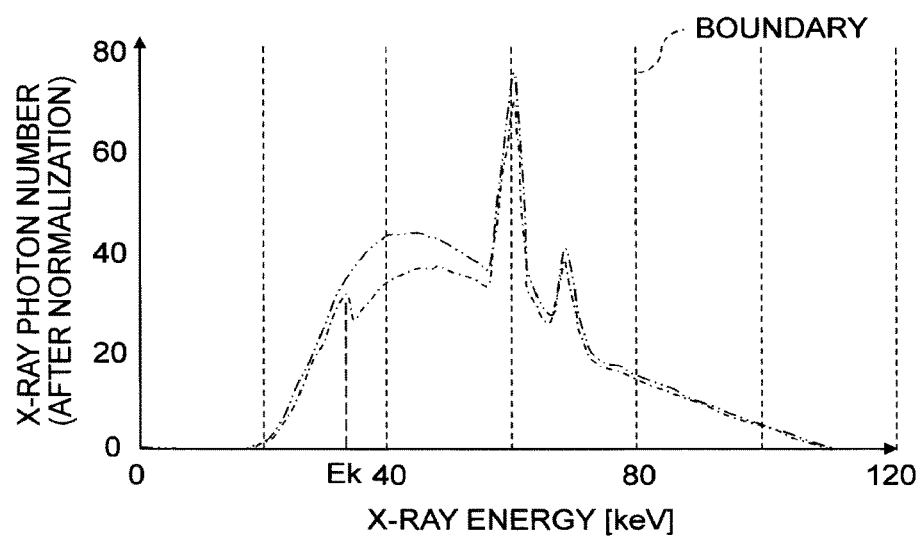
FIG. 6 shows an example of equally setting energy bands of X-ray photons to be discriminated in the X-ray detector shown in FIG. 2.

FIG. 6 shows an example of equally setting energy bands of X-ray photons to be discriminated in the X-ray detector 8 shown in FIG. 2.

In FIG. 6, the horizontal axis shows energies [keV] of X-ray photons while the vertical axis shows the normalized number of counted X-ray photons which have been emitted from the X-ray tube of the X-ray exposure part 7 and transmitted an aluminum filter having a thickness of 2.5 mm. In FIG. 6, the dashed-dotted line shows the normalized number of counted X-ray photons when iodine exists on the X-ray path while the dashed-two dotted line shows the normalized number of counted X-ray photons when iodine does not exist on the X-ray path.

As shown in FIG. 6, when iodine exists on the X-ray path, the discontinuous point corresponding to the K absorption edge of iodine appears on the X-ray spectrum. Such an X-ray spectrum can be obtained by measurement or a simulation based on design specifications. Here, when boundaries of the energy bands of X-ray photons are set at an equal interval as shown by the dotted lines, the energy Ek at the K absorption edge is included in one of the energy bands.

Thus, the threshold setting part 32 is configured to set two energy bands based on information which has been input from the input circuit 5 and specifies an X-ray absorber, such as a contrast agent. Specifically, the threshold setting part 32 has a function as an input part configured to input information, specifying an X-ray absorber of interest, such as a contrast agent, a medicine, or a device, which has been sent into the object O and exists in the object O, from the input circuit 5. The threshold setting part 32 also has a function to set two energy bands as threshold voltages applied to the comparators 24 of the X-ray detector 8 so that the energy at the K absorption edge of the X-ray absorber specified based on the input information specifying the X-ray absorber becomes the boundary of the two energy bands.

An energy spectrum near the K absorption edge also changes depending on imaging conditions, such as a tube voltage applied to the X-ray tube and a type of a beam filter, which determine radiation quality of X-rays. Thus, the threshold setting part 32 is configured to obtain imaging conditions to determine radiation quality of X-rays, such as a tube voltage applied to the X-ray tube and a type of a beam filter, from the control signal generation part 31.

Hereinafter, an example case where an X-ray absorber of interest in the object O is mainly a contrast agent will be described.

Figure 7:
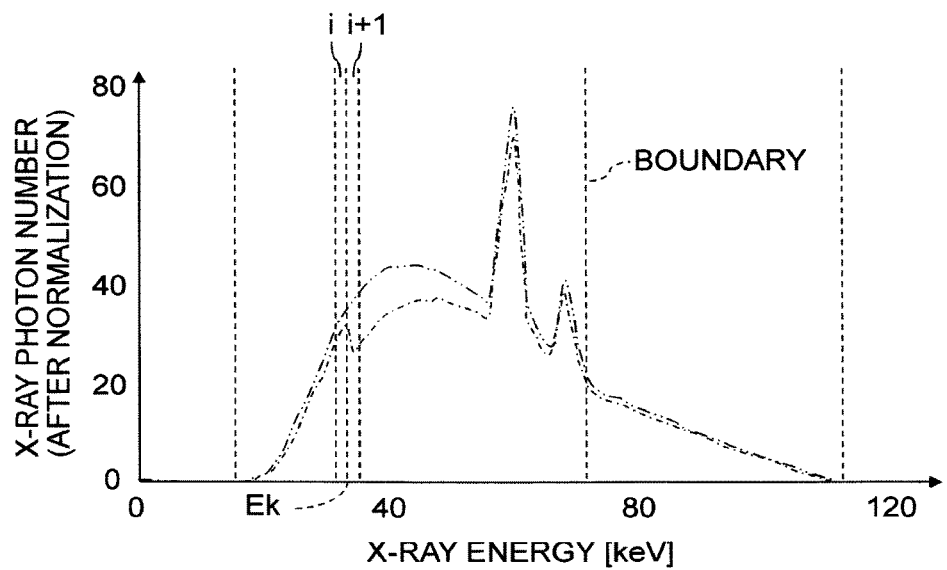
FIG. 7 shows an example of setting energy bands of X-ray photons to be discriminated in the X-ray detector shown in FIG. 2, according to the K absorption edge of iodine.

FIG. 7 shows an example of setting energy bands of X-ray photons to be discriminated in the X-ray detector 8 shown in FIG. 2, according to the K absorption edge of iodine.

In FIG. 7, the horizontal axis shows energies [key] of X-ray photons while the vertical axis shows the normalized number of counted X-ray photons which have been emitted from the X-ray tube of the X-ray exposure part 7 and transmitted an aluminum filter having a thickness of 2.5 mm. In FIG. 7, the dashed-dotted line shows the normalized number of counted X-ray photons when iodine exists on the X-ray path while the dashed-two dotted line shows the normalized number of counted X-ray photons when iodine does not exist on the X-ray path.

As shown in FIG. 7, the boundary between the i-th energy band and the (i+1)-th energy band can be made coincide with the energy Ek at the K absorption edge by adjusting threshold voltages applied to the comparators 24 of the X-ray detector 8.

Note that, energy bands of X-ray photons has conflicting requests. One request is that it is preferable to set the width of each energy band as wide as possible in order to increase the number of photons to be counted in each energy band so that quantum noises can be reduced. Conversely, the other request is that it is preferable to set the width of each energy band as narrow as possible so that a ratio of X-ray photons to be counted in the i-th and (i+1)-th two energy bands lower and higher than the energy Ek at the K absorption edge becomes large.

Thus, the threshold setting part 32 is configured to set two energy bands, i.e., the i-th and (i+1)-th energy bands bounded by the energy Ek at the K absorption edge, whose bandwidths are set so that a ratio of the numbers of respective X-ray photons counted in the two energy bands becomes large, and the number of X-ray photons counted in each of the two energy bands increases.

Figure 8:
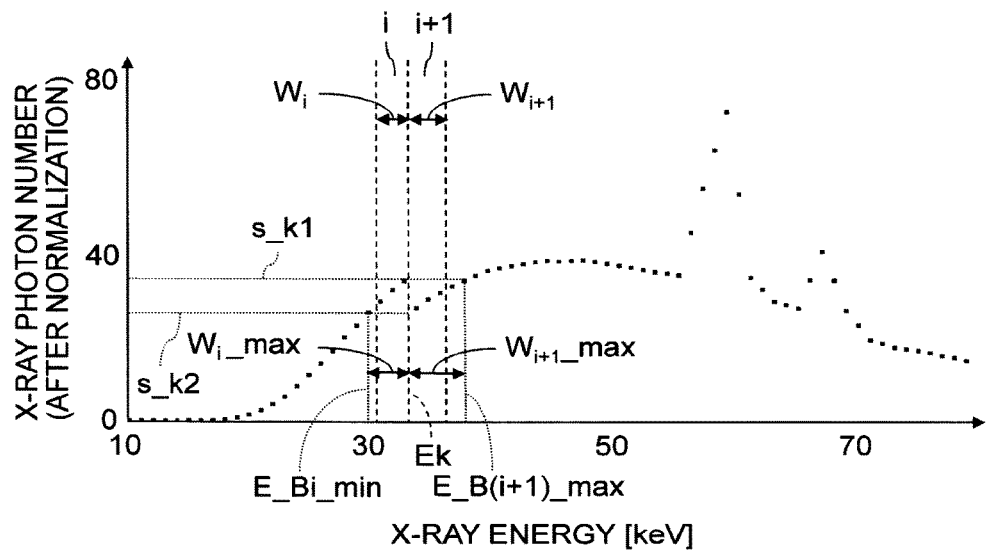
FIG. 8 shows the first example of detailed setting of two energy bands, bounded by the energy Ek at the K absorption edge, out of the energy bands shown in FIG. 7.

FIG. 8 shows the first example of detailed setting of two energy bands, bounded by the energy Ek at the K absorption edge, out of the energy bands shown in FIG. 7.

In FIG. 8, the horizontal axis shows energies [keV] of X-ray photons while the vertical axis shows the normalized number of counted X-ray photons which have been emitted from the X-ray tube of the X-ray exposure part 7 through an aluminum filter having a thickness of 2.5 mm and transmitted iodine.

As shown in FIG. 8, the maximum bandwidth $W_{i\_max}$ can be set to a width $W_i$ of the i-th energy band in the lower energy side bounded by the energy Ek at the K absorption edge. Similarly, the maximum bandwidth $W_{i+1\_max}$ can be set to a width $W_{i+1}$ of the (i+1)-th energy band in the higher energy side bounded by the energy Ek at the K absorption edge. Then, the width $W_i$ of the i-th energy band can be set to an appropriate width by setting the width $W_i$ of the i-th energy band not more than the maximum bandwidth $W_{i\_max}$. Similarly, the width $W_{i+1}$ of the (i+1)-th energy band can be set to an appropriate width by setting the width $W_{i+1}$ of the (i+1)-th energy band not more than the maximum bandwidth $W_{i+1\_max}$.

As shown in FIG. 8, the maximum bandwidth $W_{i+1\_max}$ of the (i+1)-th energy band is appropriate to be set from the energy Ek at the K absorption edge, toward the positive direction of the energy axis, to an energy E_B(i+1) max at which the number of photons becomes same as the local maximum value s_k1 of the number of X-ray photons at the K absorption edge. Meanwhile, the maximum bandwidth $W_{i\_max}$ of the i-th energy band is appropriate to be set from the energy Ek at the K absorption edge, toward the negative direction of the energy axis, to an energy E_Bi_min at which the number of photons becomes same as the local minimum value s_k2 of the number of X-ray photons at the K absorption edge.

That is, it is preferable to limit each of the width $W_i$ of the i-th energy band and the width $W_{i+1}$ of the (i+1)-th energy band to an energy range in which photons whose number is between the local maximum value s_k1 and the local minimum value s_k2 of the number of X-ray photons at the K absorption edge are emitted from the X-ray tube. When the width $W_i$ of the i-th energy band and the width $W_{i+1}$ of the (i+1)-th energy band are set by the method as described above, a ratio of the numbers of X-ray photons to be counted in the i-th and (i+1)-th energy bands can be enlarged with securing the number of the X-ray photons to be counted in each of the energy bands.

Figure 9:
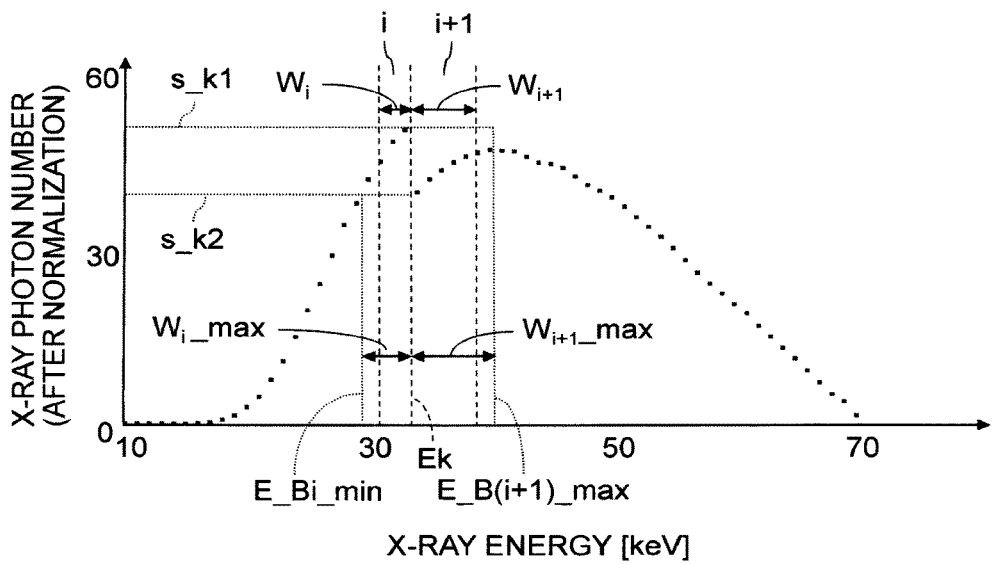
FIG. 9 shows the second example of detailed setting of two energy bands, bounded by the energy Ek at the K absorption edge, out of the energy bands shown in FIG. 7.

FIG. 9 shows the second example of detailed setting of two energy bands, bounded by the energy Ek at the K absorption edge, out of the energy bands shown in FIG. 7.

In FIG. 9, the horizontal axis shows energies [keV] of X-ray photons while the vertical axis shows the normalized number of counted X-ray photons which have been emitted from the X-ray tube of the X-ray exposure part 7 through an aluminum filter having a thickness of 2.5 mm and transmitted iodine.

As shown in FIG. 9, in a certain X-ray spectrum, the local maximum value s_k1 of the number of X-ray photons at the K absorption edge may become the maximum value of the X-ray spectrum. In that case, an energy when the number of photons becomes same as the local maximum value s_k1 of the number of X-ray photons at the K absorption edge does not exist in the higher energy side than the energy Ek at the K absorption edge. Thus, the maximum bandwidth $W_{i+1\_max}$ of the (i+1)-th energy band can be set as a predetermined width. Alternatively, the maximum bandwidth $W_{i+1\_max}$ of the (i+1)-th energy band may also be set to a width depending on an X-ray spectrum. For example, as shown in FIG. 9, the maximum bandwidth $W_{i+1\_max}$ of the (i+1)-th energy band may also be set from the energy Ek at the K absorption edge, toward the positive direction of the energy axis, to the energy E_B(i+1)_max when the number of X-ray photons becomes the local maximum value in the higher energy side than the energy Ek at the K absorption edge.

The width Wi of the i-th energy band and the width Wi+1 of the (i+1)-th energy band which should be set in the threshold setting part 32 can be previously determined for every type of contrast agent and every radiation quality of X-rays, and can be stored as a table at the threshold storage part 33. A radiation quality of X-rays is determined by a tube voltage to be applied to the X-ray tube and a type of a beam filter.

FIG. 10 shows an example of table to be stored in the threshold storage part 33 shown in FIG. 3.

As shown in FIG. 10, the appropriate width $W_i$ of the i-th energy band and the appropriate width $W_{i+1}$ of the (i+1)-th energy band related to every substance constituting an X-ray absorber, such as a contrast agent, every tube voltage to be applied to the X-ray tube, and every type of a beam filter can be stored in the threshold storage part 33. FIG. 10 shows an example case where i=1, i.e., $W_i=W_1$ and $W_{i+1}=W_2$.

Thereby, the threshold setting part 32 can input information, specifying an X-ray absorber taken into the object O, from the input circuit 5 and obtain the appropriate width $W_i$ of the i-th energy band and the appropriate width $W_{i+1}$ of the (i+1)-th energy band from the threshold storage part 33, based on the input information specifying the X-ray absorber and imaging conditions to determine radiation quality of X-rays, obtained from the control signal generation part 31. Then, boundaries of the i-th and (i+1)-th energy bands for making their widths be $W_i$ and $W_{i+1}$ respectively, energies to become the boundaries of the i-th and (i+1)-th energy bands, and threshold voltages which should be applied to the comparators 24 in order to form the boundaries can be specified.

Therefore, the threshold storage part 33 functions as an energy band storage part configured to relate each of X-ray absorbers with information for determining two X-ray energy bands depending on K absorption edges of the X-ray absorbers to store the information. Then, the threshold storage part 33 as the energy band storage part can store the information for determining the two X-ray energy bands, with further relating at least one of a tube voltage to be applied to the X-ray tube and information identifying a beam filter placed in the output side of the X-ray tube.

Meanwhile, the threshold setting part 32 is configured to obtain information for determining two energy bands corresponding to information to specify an X-ray absorber, from the threshold storage part 33 as the energy band storage part. Furthermore, when the information for determining the two X-ray energy bands stored in the threshold storage part 33 has been related with at least one of a tube voltage and information identifying a beam filter, the threshold setting part 32 is configured to refer to the threshold storage part 33 to set two energy bands based on at least one of a tube voltage and a beam filter corresponding to exposure conditions of X-rays which are exposed from the X-ray exposure part 7.

The energy bands other than the i-th and (i+1)-th energy bands bounded by the energy Ek at the K absorption edge can be determined by another method. Hereinafter, a method of determining the energy bands other than the i-th and (i+1)-th energy bands will be described.

An energy spectrum of an X-ray which is output from the X-ray tube includes not only energies near the energy Ek at the K absorption edge but also energies in a wide range, as shown in FIG. 6. Therefore, on the condition that only number counting results of X-ray photons having energies in the i-th and (i+1)-th energy bands which have been set depending on a substance constituting an X-ray absorber, such as a contrast agent, are imaged, X-rays which have energies in the other energy bands merely cause increase of radiation exposure of the object O.

Thus, it is preferable to set at least three energy bands as counting targets of the number of X-ray photons so that a number counting result of X-ray photons having energies in at least one energy band other than any of the i-th and (i+1)-th energy bands bounded by the energy Ek at the K absorption edge is also imaged. That is, imaging of all X-rays exposed to the object O leads to reduction of unnecessary radiation exposure.

An energy spectrum of an X-ray output from the X-ray tube includes the energy band lower than the i-th energy band and the energy band higher than the (i+1)-th energy band. Therefore, it is more effective to set at least four energy bands as counting targets of the number of X-ray photons for imaging.

Figure 11:
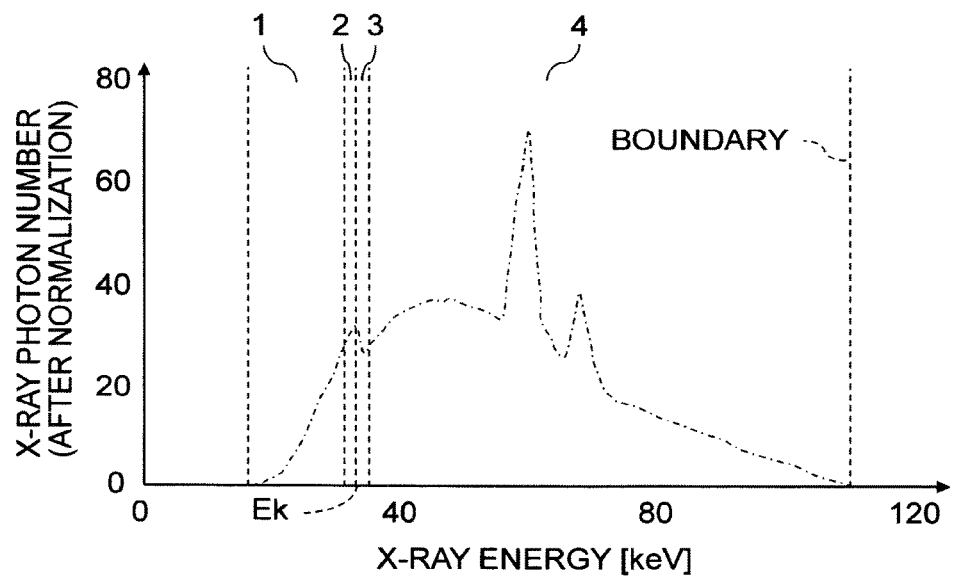
FIG. 11 shows an example of setting four energy bands, as counting targets of the number of X-ray photons, in the threshold setting part shown in FIG. 3.

FIG. 11 shows an example of setting four energy bands, as counting targets of the number of X-ray photons, in the threshold setting part 32 shown in FIG. 3.

In FIG. 11, the horizontal axis shows energies [keV] of X-ray photons while the vertical axis shows the normalized number of counted X-ray photons which have been emitted from the X-ray tube of the X-ray exposure part 7 through an aluminum filter having a thickness of 2.5 mm and transmitted iodine.

When four energy bands are set, an energy band lower than the i-th energy band and an energy band higher than the (i+1)-th energy band are set. Therefore, the energy bands bounded by the energy Ek at the K absorption edge are the second energy band and the third energy band. That is, i=2.

The lower limit of the first energy band where energies are the lowest can be set to the lower limit of an energy spectrum of an X-ray. Meanwhile, the upper limit of the fourth energy band where energies are the highest can be set to the upper limit of the energy spectrum of the X-ray. Then, also imaging and displaying data sets in the first energy band and the fourth energy band allows minimizing unnecessary radiation exposure of the object O.

The lower limit and the upper limit of an energy spectrum of an X-ray are determined depending on a tube voltage to be applied to the X-ray tube and characteristics of a beam filter. Therefore, pieces of information, for determining the first energy band and the fourth energy band, related with tube voltages and types of beam filters can be stored in the threshold storage part 33 as a table, similarly to the example shown in FIG. 10. Then, the first energy band and the fourth energy band can be determined depending on a tube voltage and a type of beam filter.

Figure 12:
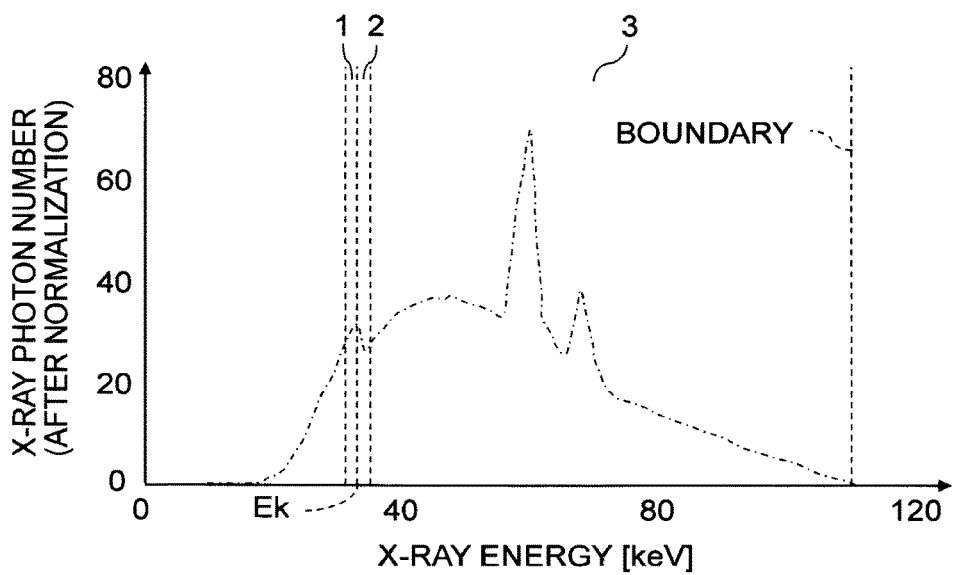
FIG. 12 shows an example of setting three energy bands, as counting targets of the number of X-ray photons, in the threshold setting part shown in FIG. 3.

FIG. 12 shows an example of setting three energy bands, as counting targets of the number of X-ray photons, in the threshold setting part 32 shown in FIG. 3.

In FIG. 12, the horizontal axis shows energies [keV] of X-ray photons while the vertical axis shows the normalized number of counted X-ray photons which have been emitted from the X-ray tube of the X-ray exposure part 7 through an aluminum filter having a thickness of 2.5 mm and transmitted iodine.

When a contrast agent is iodine, the range of the energy spectrum where energies are lower than those in the i-th energy band which is lower than the energy Ek at the K absorption edge becomes extremely small compared to the range of the energy spectrum where energies are higher than those in the (i+1)-th energy band which is higher than the energy Ek at the K absorption edge, as shown in FIG. 12.

Thus, the range of the energy spectrum where energies are higher than those in the (i+1)-th energy band may be set to an energy band to be a counting target of the number of X-ray photons, without counting the number of X-ray photons in the energy region where energies are lower than those in the i-th energy band. That is, only the i-th energy band, the (i+1)-th energy band, and the energy band where energies are higher than the (i+1)-th energy band may be imaged.

In this case, the number of energy bands to be counting targets of the number of X-ray photons is 3. Therefore, the energy bands bounded by the energy Ek at the K absorption edge are the first and the second energy bands. That is, i=1. The upper limit of the third energy band where energies are the highest can be set to the upper limit of the energy spectrum of the X-ray. Therefore, pieces of information for determining the third energy bands depending on tube voltages and the types of beam filter should be also stored in the threshold storage part 33 as a table Meanwhile, when an X-ray absorber of interest is gold, the energy Ek at the K absorption edge is near 80 keV. Therefore, when a tube voltage is 110 kV, a large part of the energy spectrum lies in a range of energies, each of which lower than the energy Ek at the K absorption edge. In such a case, opposite to the example shown in FIG. 12, it is appropriate to set the range of the energy spectrum, in which energies are lower than those in the i-th energy band, to an energy band to be a counting target of the number of X-ray photons, and not to count the number of X-ray photons in the energy region where energies are higher than those in the (i+1)-th energy band. In that case, the energy band where energies are the lowest is the first energy band, and the energy bands bounded by the energy Ek at the K absorption edge are the second and the third energy bands.

Besides the above-mentioned examples, not less than five energy bands may also be set as counting targets of the number of X-ray photons. In that case, setting the lower limit of the first energy band, in which energies are lower than energies in any other energy band, to the lower limit of the energy spectrum of X-ray, and setting the upper limit of the n-th energy band, in which energies are higher than energies in any other energy band, to the upper limit of the energy spectrum of X-ray leads to reduction of unnecessary radiation exposure of the object O. Then, at least five energy bands can be set by equally dividing at least one of the range of the energy spectrum where energies are lower than those in the i-th energy band, and the range of the energy spectrum where energies are higher than those in the (i+1)-th energy band. FIG. 7 shows an example of setting five energy bands by equally dividing the range of the energy spectrum, where energies are higher than those in the (i+1)-th energy band, into two energy bands.

Thus, at least one of energy bands where energies are higher than the two energy bands depending on the K absorption edge of an X-ray absorber of interest, and energy bands where energies are lower than the two energy bands depending on the K absorption edge of the X-ray absorber of interest can be set with an equal bandwidth. Note that, energy bands not depending on the K absorption edge can also be set in the threshold setting part 32, according to instruction information from the input circuit 5.

Although examples of making the boundary between the i-th energy band and the (i+1)-th energy band coincide with the energy Ek at the K absorption edge have been described thus far, it is also effective to set the boundary between the i-th energy band and the (i+1)-th energy band higher than the energy Ek at the K absorption edge by a predetermined amount. This is because fluctuation exists in energies of X-ray photons to be counted.

Figure 13:
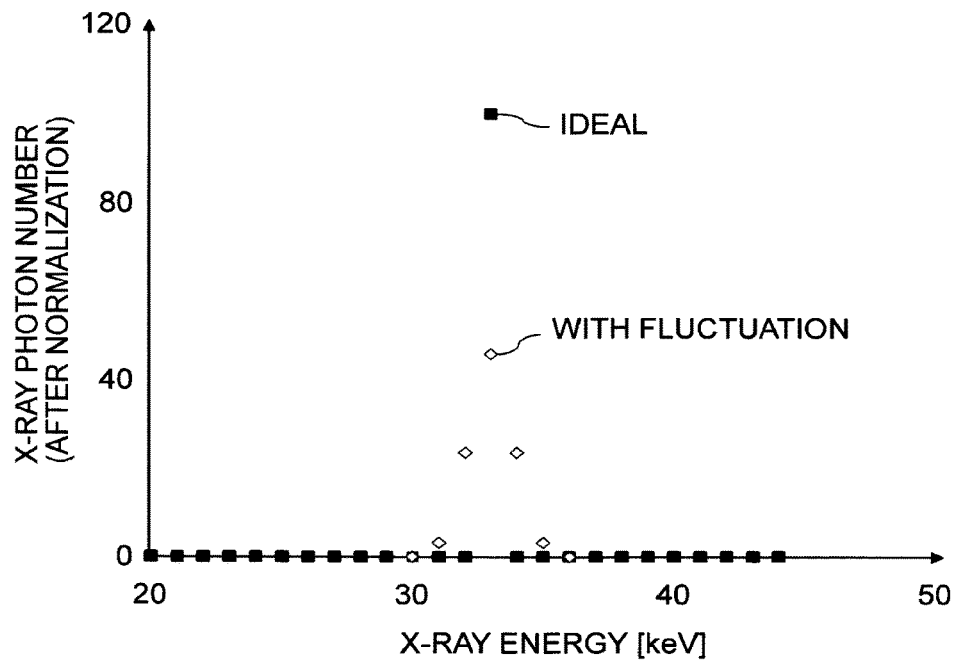
FIG. 13 shows an influence of fluctuation on a number counting result of monochromatic X-ray photons.

FIG. 13 shows an influence of fluctuation on a number counting result of monochromatic X-ray photons.

In FIG. 13, the horizontal axis shows energies [keV] of X-ray photons while the vertical axis shows the normalized number of the X-ray photons. In FIG. 13, black plotted points show ideal data and white plotted points show data actually observed with fluctuation.

As shown in FIG. 13, in the case of exposing monochromatic X-ray photons each having the energy of 33 keV, the normalized number of X-ray photons counted by a detector ideally becomes 100 at the energy of 33 keV. However, the number of X-ray photons each having the energy of 33 keV actually decreases by fluctuation, and X-ray photons having energies from 31 keV to 35 keV around the energy of 33 keV are counted.

The number of X-ray photons having a certain energy is ideally converted into electric signals having one amplitude to be counted. However, a phenomenon that amplitudes of electric signals, showing the number of X-ray photons, become slightly large or small occurs by factors, such as noises in circuits to process the electric signals and fluctuation in the number of charges generated in an X-ray detection layer. This is a factor of the fluctuation in number counting results of X-ray photons.

The above-mentioned fluctuation also arises in the case of exposing an X-ray having a continuous energy spectrum. Near the K absorption edge of a contrast agent, a certain rate of X-ray photons out of X-ray photons each having an energy lower than the energy Ek at the K absorption edge are counted as X-ray photons each having an energy higher than the energy Ek at the K absorption edge. Conversely, a certain rate of X-ray photons out of the X-ray photons each having an energy higher than the energy Ek at the K absorption edge are counted as the X-ray photons having an energy lower than the energy Ek at the K absorption edge.

That is, some of the X-ray photons each having an energy lower than the energy Ek at the K absorption edge increase the number counting result of the X-ray photons each having an energy higher than the energy Ek at the K absorption edge. Conversely, some of the X-ray photons each having an energy higher than the energy Ek at the K absorption edge increase the number counting result of the X-ray photons each having an energy lower than the energy Ek at the K absorption edge.

The number of X-ray photons to be counted in the energy band where each energy is lower than the energy Ek at the K absorption edge is more than the number of X-ray photons to be counted in the energy band where each energy is higher than the energy Ek at the K absorption edge. Therefore, influence of counted X-ray photons, each having an energy lower than the energy Ek at the K absorption edge, which are mixed in the energy band where each energy is higher than the energy Ek at the K absorption edge is larger than influence of counted X-ray photons, each having an energy higher than the energy Ek at the K absorption edge, which are mixed in the energy band where each energy is lower than the energy Ek at the K absorption edge. That is, mixing X-ray photons, each having an energy lower than the energy Ek at the K absorption edge, in the energy band where each energy is higher than the energy Ek at the K absorption edge leads to reducing a ratio between the numbers of X-ray photons whose energies are lower and higher than the K absorption edge and a contrast thereby.

Thus, it is preferable to set the boundary between the i-th energy band and the (i+1)-th energy band, which adjoin with each other, to an energy higher than the energy Ek at the K absorption edge by a predetermined amount, according to the energy Ek at the K absorption edge, so that the number of X-ray photons, each having an energy lower than the energy Ek at the K absorption edge, to be counted as X-ray photons in the energy band where each energy is higher than the energy Ek at the K absorption edge due to fluctuation is reduced. Therefore, the threshold setting part 32 has a function to set two energy bands so that the boundary of the two energy bands shifts from the energy Ek at the K absorption edge of an X-ray absorber of interest, in the higher energy side by a predetermined amount.

Figure 14:
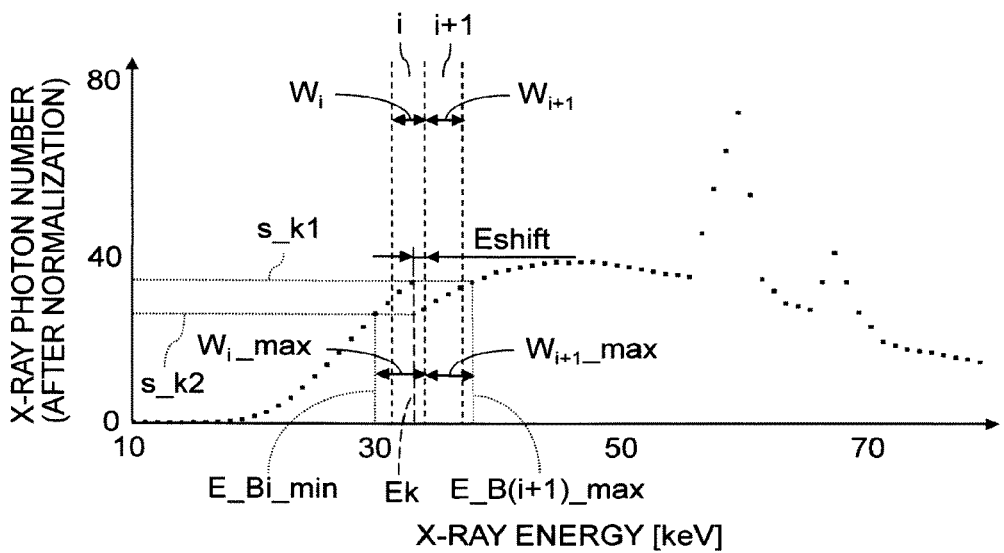
FIG. 14 shows an example of setting the i-th energy band and the (i+1)-th energy band so that influence of fluctuation is reduced, by the threshold setting part shown in FIG. 3.

FIG. 14 shows an example of setting the i-th energy band and the (i+1)-th energy band so that influence of fluctuation is reduced, by the threshold setting part 32 shown in FIG. 3.

In FIG. 14, the horizontal axis shows energies [keV] of X-ray photons while the vertical axis shows the normalized number of counted X-ray photons which have been emitted from the X-ray tube of the X-ray exposure part 7 through an aluminum filter having a thickness of 2.5 mm and transmitted iodine.

As shown in FIG. 14, the boundary between the i-th energy band and the (i+1)-th energy band which adjoin with each other can be set, according to the energy Ek at the K absorption edge, to an energy higher than the energy Ek at the K absorption edge by a predetermined amount Eshift. The predetermined amount Eshift of energy for shifting the boundary from the energy Ek at the K absorption edge can be determined empirically by measuring noises in circuits in the X-ray detector 8 or the like.

For example, when an X-ray energy spectrum observed under influence by the fluctuation shown in FIG. 13 is considered to be a Gaussian distribution and a standard deviation of the energy spectrum is σ [keV], the predetermined amount Eshift of energy can be set to kσ using an arbitrary positive coefficient k. In that case, when the positive coefficient k=1, about 68% of influence due to the fluctuation can be removed.

Setting energy bands as described above allows suppressing an increase in the number counting result of X-ray photons in the (i+1)-th energy band higher than the energy Ek at the K absorption edge, resulting from the fluctuation. Then, deterioration in a contrast which should be originally obtained can be prevented. Note that, hereinafter, an example case where the energy Ek at the K absorption edge is relatively set to the boundary between the i-th energy band and the (i+1)-th energy band will be described in order to simplify the explanation.

Although the case where a single X-ray absorber of interest is the target has been described thus far, X-ray imaging can also be performed by the K absorption edge subtraction method using a plurality of X-ray absorbers having different energies Ek at K absorption edges. In that case, the threshold setting part 32 sets plural sets of two X-ray energy bands depending on the K absorption edges of X-ray absorbers, based on information to specify the X-ray absorbers.

Figure 15:
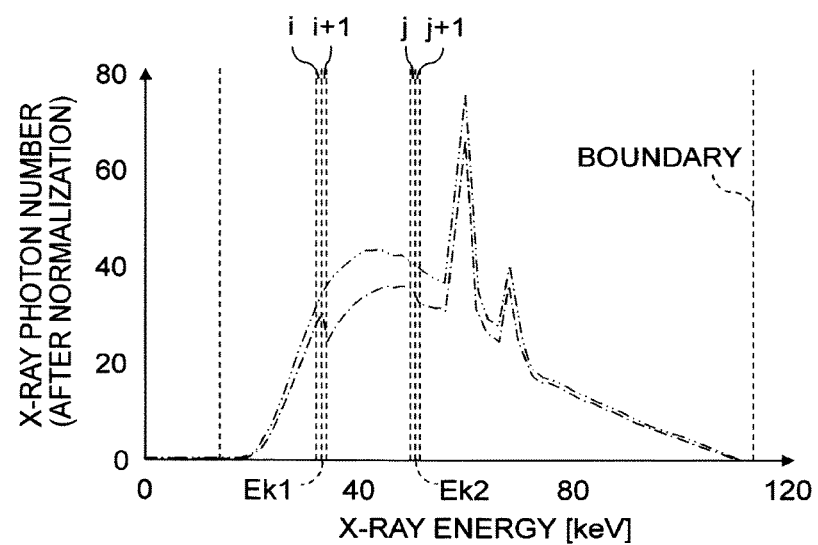
FIG. 15 shows an example of setting two sets of two X-ray energy bands, as counting targets of the number of X-ray photons, by the threshold setting part shown in FIG. 3.

FIG. 15 shows an example of setting two sets of two X-ray energy bands, as counting targets of the number of X-ray photons, by the threshold setting part 32 shown in FIG. 3.

In FIG. 15, the horizontal axis shows energies [keV] of X-ray photons while the vertical axis shows the normalized number of counted X-ray photons which have been emitted from the X-ray tube of the X-ray exposure part 7 through an aluminum filter having a thickness of 2.5 mm. In FIG. 15, the dashed-dotted line shows the normalized number of X-ray photons counted when iodine and gadolinium exist on the path of the X-ray while the dashed-two dotted line shows the normalized number of X-ray photons counted when iodine and gadolinium do not exist on the path of the X-ray.

As shown in FIG. 15, when two X-ray absorbers of iodine and gadolinium exist on the X-ray path, two K absorption edges appear on the energy spectrum of X-ray photons. Therefore, four energy bands bounded by the energies Ek1 and Ek2 corresponding to the two K absorption edges can be set as counting targets of X-ray photons. Specifically, the two energy bands consisting of the i-th and (i+1)-th energy bands bounded by the energy Ek1 corresponding to the first K absorption edge in the low energy side, and the two energy bands consisting of the j-th and (j+1)-th energy bands bounded by the energy Ek2 corresponding to the second K absorption edge in the high energy side can be set.

The energy bands outside the four energy bands, i.e. the i-th, (i+1)-th, j-th and (j+1)-th energy bands bounded by the energies Ek1 and Ek2 corresponding to the two K absorption edge may also be set as counting targets of X-ray photons for imaging, or may not be set as the counting targets. Alternatively, the energy band bands outside the four energy bands may be further divided and set as counting targets of X-ray photons.

Therefore, when two X-ray absorbers exist inside the object O, at least two sets of two X-ray energy bands depending on the K absorption edges of the two X-ray absorbers are set in the threshold setting part 32, based on information to specify the two X-ray absorbers. Then, four frames of X-ray image data corresponding to at least the two sets of the two X-ray energy bands are generated.

As described above, the threshold setting part 32 can set at least two X-ray energy bands depending on at least one K absorption edge of X-ray absorber, based on information to specify the X-ray absorber or the X-ray absorbers input from the input circuit 5. Note that, hereinafter, an example case where one X-ray absorber of interest exists inside the object O will be described in order to simplify the explanation.

The threshold setting part 32 also has a function to set energy bands for usual X-ray imaging, in addition to the above-mentioned energy bands for X-ray imaging by the K absorption edge subtraction method using an X-ray absorber, such as a contrast agent, a medicine, or a device.

It is desirable to minimize the number of energy bands which are counting targets of the number of X-ray photons, from a viewpoint of reducing a circuit size of the X-ray detector 8. Therefore, it is preferable for usual X-ray imaging to set discriminable energy bands corresponding to the number of the comparators 24 included in the X-ray detector 8 by equally dividing the energy region of an X-ray. FIG. 6 shows an example of setting five energy bands each having an equal width and the low energy band which is not a counting target of X-ray photons, according to the number of the comparators 24.

Therefore, at the time when the threshold setting part 32 sets energy bands, information to specify whether X-ray imaging is usual one or X-ray imaging by the K absorption edge subtraction method is input from the input circuit 5. Then, in the case of performing usual X-ray imaging, energy bands the number of which can be discriminated in the X-ray detector 8 are set so as to have equal widths as exemplified in FIG. 6.

Meanwhile, in the case of performing X-ray imaging by the K absorption edge subtraction method, information specifying an X-ray absorber of interest to be imaged, such as a contrast agent, a medicine, or a device, is further input from the input circuit 5. Then, the threshold setting part 32 sets energy bands depending on the energy Ek at the K absorption edge of a substance constituting the X-ray absorber.

Therefore, the threshold setting part 32 has a function to display a setting screen, as a user interface, for inputting whether X-ray imaging is one by the K absorption edge subtraction method or not and information to specify an X-ray absorber of interest by operating the input circuit 5, on the display 6. Then, the threshold setting part 32 is configured to set appropriate energy bands depending on an imaging purpose based on information input by operating the input circuit 5 through the setting screen displayed on the display 6.

When a purpose of using the X-ray diagnostic apparatus 1 is limited, inputting the information to specify an X-ray absorber of interest, such as a contrast agent, at the time of X-ray imaging may also be omitted. For example, when the X-ray diagnostic apparatus 1 is for a circulatory organ examination, a contrast agent to be used contains iodine but not barium or the like. Meanwhile, when the X-ray diagnostic apparatus 1 is for a digestive tract examination, a contrast agent to be used contains barium but not iodine or the like. Therefore, an X-ray absorber of interest may also be specified at the time of installation or a periodical inspection of the X-ray diagnostic apparatus 1. In this case, information input to the threshold setting part 32 through a user interface in order to set energy bands is only information to select whether X-ray imaging is usual X-ray imaging or X-ray imaging by the K absorption edge subtraction method.

Meanwhile, even when a purpose of using the X-ray diagnostic apparatus 1 is not limited, a contrast agent to be injected into the object O can be specified so long as inspection items of X-ray contrast examination can be specified. Therefore, when an X-ray absorber of interest is a contrast agent, at least one of examination items and information to specify the contrast agent can be input to the threshold setting part 32, as information to specify the X-ray absorber. Thereby, appropriate energy bands depending on a type of the contrast agent can be set in the threshold setting part 32 based on at least one of the examination items and the information to specify the contrast agent.

The subtraction processing part 30 has a function to generate subtraction image data by subtraction processing between a number counting signal which shows a number counting result at each pixel of X-ray photons in the i-th energy band set in the threshold setting part 32 and a number counting signal which shows a number counting result at each pixel of X-ray photons in the (i+1)-th energy band set in the threshold setting part 32. The subtraction processing part 30 also has a function to generate X-ray image data showing the thickness of an X-ray absorber of interest, such as a contrast agent, by processing including the subtraction processing. That is, the subtraction processing part 30 has a function to generate at least one frame of X-ray image data, in which an X-ray absorber of interest has been depicted, by data processing including the subtraction processing between two X-ray detection data sets corresponding to the i-th energy band and the (i+1)-th energy band respectively.

Note that, it is desirable to perform logarithmic conversion processing and normalization processing of each number counting signal before the subtraction processing. Specifically, it is desirable to perform the subtraction processing between the two X-ray detection data sets after the logarithmic conversion. In addition, it is desirable to perform the subtraction processing between the two X-ray detection data sets after the normalization performed substantially using the bandwidths $W_i$ and $W_{i+1}$ of the two energy bands. When the normalization is performed after the logarithmic conversion, the normalization can also be performed as subtraction.

Hereinafter, generation processing of subtraction image data and X-ray image data showing the thickness of a contrast agent will be described.

When the widths $W_i$ and $W_{i+1}$ of the i-th and (i+1)-th energy bands are set according to the K absorption edge, a number counting signal $C_i(xp, xc)$ at one pixel of X-ray photons in the i-th energy band and a number counting signal $C_{i+1}(xp, xc)$ at one pixel of X-ray photons in the (i+1)-th energy band are expressed by expression (8) and expression (9), respectively.

$$C_i(xp,xc) = \int_i dE \cdot \varphi(E) \cdot Matt(E) \cdot Patt(E,xp) \cdot Catt(E,xc) \cdot Dabs(E,xd) \quad (8)$$

$$C_{i+1}(xp,xc) = \int_{i+1} dE \cdot \varphi(E) \cdot Matt(E) \cdot Patt(E,xp) Catt(E,xc) \cdot Dabs(E,xd) \quad (9)$$

wherein
E: an energy of an X-ray photon,
$\int_i dE$: integration from $E_{i1}$ to $E_{i2}$,
$E_{i1}$: the minimum value of the i-th energy band,
$E_{i2}$: the maximum value of the i-th energy band,
$\int_{i+1} dE$: integration from $E_{(i+1)1}$ to $E_{(i+1)2}$,
$E_{(i+1)1}$: the minimum value of the (i+1)-th energy band, and
$E_{(i+1)2}$: the maximum value of the (i+1)-th energy band.

Since the function in the integration in expression (8) is continuous, an energy $E_i$ ($E_{i1} < E_i < E_{i2}$) of an X-ray photon which satisfies expression (10) exists. Note that, $W_i = E_{i2} - E_{i1}$.

$$C_i(xp,xc) = \varphi(E_i) \cdot W_i \cdot Matt(E_i) \cdot Patt(E_i,xp) \cdot Catt(E_i,c) \cdot Dabs(E_i,xd) \quad (10)$$

Similarly, since the function in the integration in expression (9) is continuous, an energy $E_{i+1}$ ($E_{(i+1)1} < E_{i+1} < E_{(i+1)2}$) of an X-ray photon which satisfies expression (11) exists. Note that, $W_{i+1} = E_{(i+1)2} - E_{(i+1)1}$.

$$C_{i+1}(xp,xc) = \varphi(E_{i+1}) \cdot W_{i+1} \cdot Matt(E_{i+1}) \cdot Patt(E_{i+1},xp) \cdot Catt(E_{i+1},xc) \cdot Dabs(E_{i+1},xd) \quad (11)$$

In expression (10) and expression (11), $\varphi(E_i) \cdot W_i$ and $\varphi(E_{i+1}) \cdot W_{i+1}$ correspond to the numbers of photons in the energy bands $W_i$ (=$E_{i2} - E_{i1}$) and $W_{i+1}$ (=$E_{(i+1)2} - E_{(i+1)1}$), respectively. Furthermore, the boundaries $E_{i1}$, $E_{i2}$, $E_{(i+1)1}$, and $E_{(i+1)2}$ of the i-th and (i+1)-th energy bands, i.e. the widths $W_i$ and $W_{i+1}$ of the energy bands can be determined depending on an element constituting a contrast agent, a tube voltage to be applied to the X-ray tube, and a type of a beam filter, as shown in FIG. 10.

The subtraction image data can be generated by subtraction processing between the number counting signals $C_i$(xp, xc) and $C_{i+1}$(xp, xc), shown by expression (10) and expression (11), as the number counting results of X-ray photons in the two adjacent energy bands bounded by the energy Ek at the K absorption edge. Note that, it is desirable to perform the logarithmic conversion processing before the subtraction processing, as described above.

This is because an X-ray has a characteristic of attenuating exponentially due to the object O and a contrast agent. The number counting results of X-ray photons correspond to the total attenuation rate of an X-ray, which is a product of an attenuation rate of the X-ray due to the object O and an attenuation rate of the X-ray due to a contrast agent, as shown in expression (10) and expression (11). Thus, in the case of generating subtraction image data, the attenuation rate of X-ray due to the object O and the attenuation rate of X-ray due to the contrast agent can be converted from a product to a sum by logarithmic conversion, prior to the subtraction processing. Thereby, the number counting results of X-ray photons corresponding to the thickness of a contrast agent, from which influences of the thickness of the object O and the attenuation rate of X-ray due to the object O have been reduced, can be obtained as the number counting signals $C_i$(xp, xc) and $C_{i+1}$(xp, xc).

Furthermore, since the widths $W_i$ and $W_{i+1}$ of the two adjacent energy bands bounded by the energy Ek at the K absorption edge are different from each other, it is desirable to normalize the number counting signals $C_i$(xp, xc) and $C_{i+1}$(xp, xc), from the X-ray detector 8, by the widths $W_i$ and $W_{i+1}$ of the energy bands. That is, the subtraction image data can be generated using the numbers of X-ray photons per unit energy, by normalization processing for dividing the number counting results of X-ray photons in the energy bands by the widths $W_i$ and $W_{i+1}$ of the energy bands, respectively.

Therefore, the subtraction image data Sub(xp, xc) can be obtained by the first one of expressions (12).

$$\begin{aligned}
Sub(xp, xc) &= \ln\{C_i(xp, xc)/W_i\} - \ln\{C_{i+1}(xp, xc)/W_{i+1}\} \\
&= \ln[\{\varphi(E_i) \cdot Matt(E_i) \cdot Patt(E_i, xp) \cdot Catt(E_i, xc) \cdot \\
&\quad Dabs(E_i, xd)\}/\{\varphi(E_{i+1}) \cdot Matt(E_{i+1}) \cdot \\
&\quad Patt(E_{i+1}, xp) \cdot Catt(E_{i+1}, xc) \cdot Dabs(E_{i+1}, xd)\}] \\
&= \ln\{\varphi(E_i)/\varphi(E_{i+1}) \cdot Matt(E_i)/Matt(E_{i+1}) \cdot \\
&\quad Patt(E_i, xp)/Patt(E_{i+1}, xp) \cdot Catt(E_i, xc)/ \\
&\quad Catt(E_{i+1}, xc) \cdot Dabs(E_i, xd)/Dabs(E_{i+1}, xd)\}
\end{aligned} \quad (12)$$

When the fourth term $Catt(E_i, xc)/Catt(E_{i+1}, xc)$ with regard to a contrast agent in the last expression of expression (12) is separated from the other terms, i.e. the first term $\varphi(E_i)/\varphi(E_{i+1})$, the second term $Matt(E_i)/Matt(E_{i+1})$, the third term $Patt(E_i, xp)/Patt(E_{i+1}, xp)$, and the fifth term $Dabs(E_i, xd)/Dabs(E_{i+1}, xd)$, and the product of the first term $\varphi(E_i)/\varphi(E_{i+1})$, the second term $Matt(E_i)/Matt(E_{i+1})$, the third term $Patt(E_i, xp)/Patt(E_{i+1}, xp)$, and the fifth term $Dabs(E_i, xd)/Dabs(E_{i+1}, xd)$ is indicated by $\alpha(E_i, E_{i+1}, xp, xd)$, expression (12) becomes expression (13).

$$Sub(xp,c) = \ln\{Catt(E_i,xc)/Catt(E_{i+1},xc)\} + \ln\{\alpha(E_i,E_{i+1},xp,xd)\} \quad (13)$$

Unless a contrast agent and the anode of the X-ray tube consist of substances whose atomic numbers are close to each other, the X-ray spectrum may be considered to change continuously between energies lower and higher than the K absorption edge of the contrast agent. For example, the atomic number of iodine is 53, the atomic number of xenon is 54, the atomic number of barium is 56, and the atomic number of gadolinium is 64, each of which is used as a contrast agent. Furthermore, the atomic number of gold used as a part of medicine or a device is 79.

By contrast, the atomic number of molybdenum is 42, the atomic number of rhodium is 45, and the atomic number of tungsten is 74, each of which is generally used as the anode of the X-ray tube. Furthermore, the energy at the K absorption edge of molybdenum is 20.008 keV, the energy at the K absorption edge of rhodium is 23.230 keV, and the energy at the K absorption edge of tungsten is 69.533 keV.

Therefore, it may be considered that a contrast agent and the anode of the X-ray tube do not consist of substances whose atomic numbers are close to each other.

The second term $Matt(E_i)/Matt(E_{i+1})$, the third term $Patt(E_i, xp)/Patt(E_{i+1}, xp)$, and the fifth term $Dabs(E_i, xd)/Dabs(E_{i+1}, xd)$ in the last expression of expression (12) are terms with regard to substances of which characteristics change continuously between energies lower and higher than the K absorption edge of a contrast agent.

Therefore, when the energy $E_i$ ($E_{i1} < E_i < E_{i2}$) in the negative side than the K absorption edge and the energy $E_{i+1}$ ($E_{(i+1)1} < E_{i+1} < E_{(i+1)2}$) in the positive side than the K absorption edge have values very close to each other, the product $\alpha(E_i, E_{i+1}, xp, xd)$ of the first term $\varphi(E_i)/\varphi(E_{i+1})$, the second term $Matt(E_i)/Matt(E_{i+1})$, the third term $Patt(E_i, xp)/Patt(E_{i+1}, xp)$, and the fifth term $Dabs(E_i, xd)/Dabs(E_{i+1}, xd)$ becomes a value close to 1.

Meanwhile, when the energy $E_i$ in the negative side than the K absorption edge and the energy $E_{i+1}$ in the positive side than the K absorption edge do not have values very close to each other, the product $\alpha(E_i, E_{i+1}, xp, xd)$ becomes a value having a certain size. When the thickness xp of the object O is known, the other parameters have quantities specific to the apparatus. Therefore, the product $\alpha(E_i, E_{i+1}, xp, xd)$ can be previously obtained by calibration.

Therefore, as shown in expression (14), only the first term of the right side of expression (13) can be imaged.

$$\ln\{Catt(E_i,xc)/Catt(E_{i+1},xc)\} = Sub(xp,xc) - \ln\{\alpha(E_i,E_{i+1},xp,xd)\} \quad (14)$$

In the X-ray image data generated as values of the left side of expression (14), a pixel value at each pixel on which a contrast agent does not exist becomes zero. Therefore, X-ray image data in which a contrast agent has been enhanced can be obtained with a high contrast.

In expression (14), the X-ray absorption characteristic $Catt(E_i, xc)$, corresponding to the energy Ei, by a contrast agent is expressed by expression (15) similarly to expression (6).

$$Catt(E_i, xc) = \exp\{-\mu c(E_i) \cdot xc\} \qquad (15)$$

Thus, the left side of expression (14) becomes expression (16).

$$\ln\{Catt(E_i, xc)/Catt(E_{i+1}, xc)\} = \ln[\exp\{-\mu c(E_i) \cdot xc\}/ \qquad (16)$$
$$\exp\{-\mu c(E_{i+1}) \cdot xc\}]$$
$$= \{-\mu c(E_i) + \mu c(E_{i|1})\} \cdot xc$$

Therefore, expression (14) becomes expression (17).

$$\{\mu c(E_i) \cdot \mu c(E_{i+1})\} \cdot xc = \text{Sub}(xp, c) - \ln\{\alpha(E_i, E_{i+1}, xp, xd)\} \qquad (17)$$

The thickness xc of a contrast agent can be obtained by expression (18) from expression (17).

$$xc = [\text{Sub}(xp, xc) - \ln\{\alpha(E_i, E_{i+1}, xp, xd)\}]/ \qquad (18)$$
$$\{-\mu c(E_i) + \mu c(E_{i+1})\}$$
$$= \ln\{C_i(xp, xc)/W_i\} - \ln\{C_{i+1}(xp, xc)/W_{i+1}\}$$
$$-\ln\{\alpha(E_i, E_{i+1}, xp, xd)\}]/$$
$$\{-\mu c(E_i) + \mu c(E_{i+1})\}$$
$$= \ln\{C_i(xp, xc)\} - \ln\{C_{i+1}(xp, xc)\} -$$
$$\{\ln(W_i) - \ln(W_{i+1})\} - \ln\{\alpha(E_i, E_{i+1}, xp, xd)\}]/$$
$$\{-\mu c(E_i) + \mu c(E_{i+1})\}$$

As shown by expression (18), the subtraction of the logarithmic conversion results of the widths $W_i$ and $W_{i+1}$ of the energy bands and the value $\alpha(E_i, E_{i+1}, xp, xd)$ specific to the apparatus are subtracted from the subtraction of logarithmic conversion results of the number counting signal $C_i(xp, xc)$ and the number counting signal $C_{i+1}(xp, xc)$, which are output from the X-ray detector 8. Furthermore, the subtraction result is divided by a difference between the X-ray absorption coefficients $\mu c(E_i)$ and $\mu c(E_{i+1})$ of the energy levels $E_i$ and $E_{i+1}$, which have been set to be lower and higher than the K absorption edge of the contrast agent. Thereby, the thickness xc of the contrast agent can be obtained as information specific to the contrast agent. The thicknesses xc of the contrast agent at pixels are image data in which the presence of the contrast agent is enhanced, similarly to image data shown by expression (14). Specifically, the image data shown by expression (18) are image information in which each pixel value shows the thickness xc of the contrast agent.

The absorption coefficient storage part 36 stores the X-ray absorption coefficients $\mu c(E_i)$ and $\mu c(E_{i+1})$ for every substance constituting an X-ray absorber, such as a contrast agent. Meanwhile, the subtraction processing part 30 is configured to obtain the corresponding X-ray absorption coefficients $\mu c(E_i)$ and $\mu c(E_{i+1})$ from the absorption coefficient storage part 36, based on information, specifying the X-ray absorber, obtained from the input circuit 5 through the threshold setting part 32, in the case of calculating the thickness xc of the contrast agent by the operation shown by expression (18).

In expression (18), the value $\alpha(E_i, E_{i+1}, xp, xd)$ specific to the apparatus changes depending on a variety of conditions including a pixel position, a tube voltage to be applied to the X-ray tube, a type of a beam filter, an X-ray absorber, such as the bed 10 or press plates used for a breast imaging apparatus, the thickness of the object O which X-rays transmit, elements constituting a contrast agent, and a type and thickness of a detection layer of the X-ray detector 8. Thus, these conditions will be described in detail.

As described above, the value $\alpha(E_i, E_{i+1}, xp, xd)$ specific to the apparatus is the product of the first term $\varphi(E_i)/\varphi(E_{i+1})$, the second term $Matt(E_i)/Matt(E_{i+1})$, the third term $Patt(E_i, xp)/Patt(E_{i+1}, xp)$, and the fifth term $Dabs(E_i, xd)/Dabs(E_{i+1}, xd)$ in the last expression of expression (12).

The number $\varphi(E)$ of X-ray photons, each having an energy E, exposed from the X-ray tube toward each pixel, which determines the value of the first term $\varphi(E_i)/\varphi(E_{i+1})$, differs for every pixel. This is because the intensity of an X-ray exposed from the X-ray tube has spatial non-uniformity. That is, the number $\varphi(E)$ of X-ray photons each having an energy E differs depending on a spatial position.

The tube voltage applied to the X-ray tube may be arbitrarily set by a user. Alternatively, the tube voltage of the X-ray tube is automatically controlled according to previously defined imaging conditions. Therefore, the tube voltage applied to the X-ray tube is not usually constant. When the tube voltage of the X-ray tube changes, the shape of an X-ray energy spectrum changes depending on the tube voltage. Thereby, the value of the first term $\varphi(E_i)/\varphi(E_{i+1})$ in the last expression of expression (12) changes depending on the tube voltage applied to the X-ray tube.

Furthermore, a beam filter is placed near the exposure port of the X-ray tube. The beam filter takes a role to adjust an X-ray energy spectrum exposed to the object O. The beam filter often uses a metallic foil having a uniform thickness. However, the thickness of the beam filter is not completely uniform. Therefore, spatial non-uniformity exists in the intensity of an X-ray having transmitted the beam filter. In addition, transmission characteristic of the beam filter differ slightly depending on the X-ray energy $E_i$ or $E_{i+1}$. Thus, the number $\varphi(E)$ of X-ray photons having an energy E and the value of the first term $\varphi(E_i)/\varphi(E_{i+1})$ in the last expression of expression (12) differ depending on a spatial position due to influence of the beam filter.

Strictly speaking, the thickness of each X-ray absorber, such as the bed 10 and press plates, which exists between the X-ray exposure part 7 and the X-ray detector 8 differs for every position. Furthermore, X-ray transmission characteristic of each X-ray absorber differ slightly depending on the X-ray energy $E_i$ or $E_{i+1}$. Thus, the value of the second term $Matt(E_i)/Matt(E_{i+1})$ in the last expression of expression (12) differs depending on a spatial position. Note that, in the case of exchanging an X-ray absorber, such as a press plate, according to an inspection purpose, the value of the second term $Matt(E_i)/Matt(E_{i+1})$ in the last expression of expression (12) changes depending on an X-ray absorber to be placed.

The thickness xp of the object O differs for every position. Furthermore, X-ray transmission characteristic of the object O differ slightly depending on the X-ray energy $E_i$ or $E_{i+1}$. Thus, the value of the third term $Patt(E_i, xp)/Patt(E_{i+1}, xp)$ in the last expression of expression (12) differs depending on a position of the object O, that is, a spatial position.

The energy Ek at the K absorption edge differs for every material of a contrast agent. Therefore, the X-ray energies $E_i$ and $E_{i+1}$, which are set to be lower and higher than the energy Ek at the K absorption edge, differ depending on the material of the contrast agent. Thus, each value of the first term $\varphi(E_i)/\varphi(E_{i+1})$, the second term $Matt(E_i)/Matt(E_{i+1})$, the third term $Patt(E_i, xp)/Patt(E_{i+1}, xp)$, and the fifth term $Dabs(E_i, xd)/Dabs(E_{i+1}, xd)$ in the last expression of expression (12) changes depending on the material of the contrast agent.

A type and thickness of the X-ray detection layer of the X-ray detector 8 also influence the value $\alpha(E_i, E_{i+1}, xp, xd)$. For example, the value $\alpha(E_i, E_{i+1}, xp, xd)$ is a function of the thickness xd of the X-ray detection layer. Thus, when the X-ray detector 8 is exchanged for another detector of which the thickness xd of an X-ray detection layer is different from that of the X-ray detector 8, the value $\alpha(E_i, E_{i+1}, xp, xd)$ changes. Furthermore, when the material of the X-ray detection layer changes by the exchange of the X-ray detector 8, the value $\alpha(E_i, E_{i+1}, xp, xd)$ also changes.

As described above, the value $\alpha(E_i, E_{i+1}, xp, xd)$ changes depending on a variety of conditions. Therefore, each pixel value of the enhanced image data $\ln \{Catt(E_i, xc)/Catt(E_{i+1}, xc)\}$ of a contrast agent obtained by expression (14) and each pixel value of image data obtained as the thickness xc of the contrast agent by expression (18) change depending on the above-mentioned conditions even when the thickness xc of the contrast agent is constant. That is, each image level of the contrast enhanced image data $\ln \{Catt(E_i, xc)/Catt(E_{i+1}, xc)\}$ varies depending on conditions including a pixel position, imaging conditions, such as a tube voltage and a beam filter, X-ray absorbers, such as the bed 10 and press plates, the thickness xp of the object O, a material and the thickness xd of the detection layer of the X-ray detector 8, and elements constituting the contrast agent.

The variation in the image levels of the enhanced image data $\ln \{Catt(E_i, xc)/Catt(E_{i+1}, xc)\}$ of the contrast agent and image data in which the thickness xc of the contrast agent is each pixel value can be reduced using the value $\alpha(E_i, E_{i+1}, xp, xd)$ at each case, which has previously been obtained by calibration. A specific procedure is described below. In the calibration, a phantom, such as an acrylic board, simulating a human body is set as the object O, and X-ray imaging is performed without using a contrast agent.

When a contrast agent is not used, the thickness of the contrast agent is xc=0. In addition, the transmittance of X-ray to a contrast agent becomes 100%. Therefore, expression (19) is satisfied.

$$Catt(E_i, 0) = Catt(E_{i+1}, 0) \quad (19)$$

Therefore, the subtraction processing shown in expression (13) becomes as shown in expression (20).

$$\begin{aligned} Sub(xp, 0) &= \ln\{Catt(E_i, 0)/Catt(E_{i+1}, 0)\} + \\ &\quad \ln\{\alpha(E_i, E_{i+1}, xp, xd)\} \\ &= \ln\{\alpha(E_i, E_{i+1}, xp, xd)\} \end{aligned} \quad (20)$$

When non-contrast X-ray imaging using a phantom is performed for plural conditions, and subsequently, the operation shown by the first expression of expression (12) is performed, the values of $\ln \{\alpha(E_i, E_{i+1}, xp, xd)\}$ corresponding to the conditions can be obtained by expression (20). Specifically, the value of $\ln \{\alpha(E_i, E_{i+1}, xp, xd)\}$ can be obtained according to conditions including a pixel position, imaging conditions, such as a tube voltage and a beam filter, X-ray absorbers, such as the bed 10 and press plates, the thickness xp of the object O, a material and the thickness xd of the detection layer of the X-ray detector 8, which influence the image levels of the enhanced image data $\ln \{Catt(E_i, xc)/Catt(E_{i+1}, xc)\}$ of the contrast agent and image data in which each pixel value is the thickness xc of the contrast agent.

As a specific example, X-ray imaging and the subtraction processing shown by expression (20) can be performed with changes of imaging conditions, e.g., setting the tube voltage to different values, such as 50, 60, 70, 80, 90, 100, and 110 kV, using an aluminum (Al) filter and a tantalum (Ta) filter sequentially as a beam filter, placing the bed 10 and a press plate which can be used, sequentially setting phantoms having thicknesses, such as 5, 10, 15, 20, 25, and 30 cm, and exchanging the X-ray detector 8 for another X-ray detector which can be used. Furthermore, X-ray imaging is performed under each imaging condition, with sequentially setting energy bands of X-ray photons corresponding to the K absorption edges of a variety of elements constituting a contrast agent, such as iodine, barium, gold, and gadolinium, a medicine, and a device.

Then, the values of $\ln \{\alpha(E_i, E_{i+1}, xp, xd)\}$ corresponding to plural conditions can be obtained for each of X-ray absorbers, such as contrast agents, medicines, and devices. The function to obtain the values of $\ln \{\alpha(E_i, E_{i+1}, xp, xd)\}$ can be provided with the subtraction processing part 30. Furthermore, the values of $\ln \{\alpha(E_i, E_{i+1}, xp, xd)\}$ obtained by the subtraction processing part 30 can be related to the respective conditions and the respective X-ray absorbers, such as contrast agents, and stored as a table in the calibration data storage part 35. Note that, since the value of $\ln \{\alpha(E_i, E_{i+1}, xp, xd)\}$ is calculated for every pixel, the values of $\ln \{\alpha(E_i, E_{i+1}, xp, xd)\}$ at pixels become reference data having two dimensional pixel values similar to image data.

Then, the subtraction processing part 30 is configured to be able to calculate the thickness xc of the contrast agent shown by expression (18) with referring to the reference data stored in the calibration data storage part 35 when X-ray contrast imaging of the object O is performed. Specifically, the subtraction processing part 30 can perform the operation, shown by expression (18), by obtaining a value of $\ln \{\alpha(E_i, E_{i+1}, xp, xd)\}$ corresponding to imaging conditions nearest to the conditions of the X-ray contrast imaging and an X-ray absorber used for the X-ray contrast imaging, out of the values of $\ln \{\alpha(E_i, E_{i+1}, xp, xd)\}$ stored as reference data sets corresponding to imaging conditions and X-ray absorbers, such as contrast agents, in the calibration data storage part 35. Note that, conditions for X-ray imaging for specifying the reference data can be acquired from the control signal generation part 31. Thereby, X-ray image data showing the thicknesses xc of the contrast agent can be generated.

Therefore, the calibration data storage part 35 has a function as a reference data storage part which is configured to store reference data sets related to X-ray absorbers, such as contrast agents, and imaging conditions. Then, the subtraction processing part 30 is configured to generate X-ray image data, showing the thicknesses xc of an X-ray absorber of interest, by referring to a reference data set, related to a corresponding X-ray absorber and corresponding imaging conditions, out of the reference data sets stored in the calibration data storage part 35.

The X-ray image generation part 34 has a function to generate X-ray image data based on number counting results of X-ray photons in the respective energy bands, which have been output from the X-ray detector 8 in usual X-ray imaging. In addition, the X-ray image generation part 34 also has a function to generate X-ray image data based on number counting results of X-ray photons counted in all energy bands which have been set for X-ray imaging by the K absorption edge subtraction method. The X-ray image data can be image data in which number counting signals of X-ray photons, output from the X-ray detector 8, are pixel values. Alternatively, the X-ray image data can also be image data in which the thicknesses of the object O or the contrast agent, extracted based on the number counting signals, are pixel values.

Since the number counting signal of X-ray photons is obtained for each energy band, X-ray image data are also generated for each energy band. Thus, one frame of X-ray image data common to different energy bands can be generated by weighted-averaging of frames of X-ray image data corresponding to the energy bands. Alternatively, one frame of X-ray image data common to different energy bands can also be obtained by selecting one typical frame of X-ray image data out of frames of X-ray image data corresponding to the energy bands.

Specifically, when the threshold setting part 32 has set not less than three energy bands including at least one energy band other than two energy bands for X-ray imaging by the K absorption edge subtraction method, the X-ray image generation part 34 can generate X-ray image data, of which contrast does not correspond to the K absorption edge, based on X-ray detection data corresponding to at least one energy region out of the at least three set energy bands. In other words, when the threshold setting part 32 has set a single energy band or a plurality of energy bands which do not depend on the K absorption edge, the X-ray image generation part 34 can generate X-ray image data, having a contrast which does not correspond to the K absorption edge, based on X-ray detection data corresponding to at least one energy band which do not depend on the K absorption edge.

The image data storage part 37 is a storage circuit for storing X-ray image data generated in each element, such as the subtraction processing part 30 and the X-ray image generation part 34, of the medical image processing apparatus 15. Note that, when X-ray image data stored in the image data storage part 37 correspond to a specific energy band, it is preferable to attach information to specify the energy band, as incidental information, with the X-ray image data. The incidental information for specifying an energy band can be generated in an element, such as the subtraction processing part 30 or the X-ray image generation part 34, which generates X-ray image data.

The image composition part 38 has a function to combine subtraction image data or image data showing the thicknesses of a contrast agent, generated in the subtraction processing part 30 in X-ray imaging by the K absorption edge subtraction method, with X-ray image data generated by the X-ray image generation part 34 based on number counting results of X-ray photons in all the energy bands. That is, the image composition part 38 can combine X-ray image data, in which an X-ray absorber of interest has been depicted, with X-ray image data having a contrast which does not correspond to the K absorption edge of the X-ray absorber.

The composite image data Img of the subtraction image data Img_ke and the X-ray image data Img_tot common to all the energy bands can be generated by expression (21) using weights $\omega 1$ and $\omega 2$.

$$Img = \omega 1 \cdot Img\_ke + \omega 2 \cdot Img\_tot \quad (21)$$

That is, the composite image data Img can be generated by weighting addition processing of the subtraction image data Img_ke and the X-ray image data Img_tot common to all the energy bands. The weights $\omega 1$ and $\omega 2$ for the weighting addition processing can be set arbitrarily.

The filter processing part 40 has a function to perform filter processing for reducing noise, of subtraction image data or image data showing the thicknesses of the contrast agent, prior to the composition processing of X-ray image data sets in the image composition part 38. A noise reduction filter can be an arbitrary filter, such as a filter in spatial directions, a filter in the time direction, a linear filter, and a nonlinear filter, such as a morphological filter.

The compression processing part 39 has a function to perform compression processing of a dynamic range of X-ray image data to be combined with the subtraction image data or the image data showing the thicknesses of a contrast agent in the image composition part 38.

The display processing part 41 has a function to perform necessary display processing of X-ray image data generated in each element, such as the subtraction processing part 30, the X-ray image generation part 34, and the image composition part 38, of the medical image processing apparatus 15 and X-ray image data stored in the image data storage part 37, and to display the X-ray image data after the display processing on the display 6. Note that, subtraction image data generated in the subtraction processing part 30 in X-ray imaging by the K absorption edge subtraction method and X-ray image data generated by the X-ray image generation part 34 based on number counting results of X-ray photons in all the energy bands may also be displayed in parallel on the display 6 without composition.

(Operation and Action)

Next, an operation and action of the X-ray diagnostic apparatus 1 will be described. A case of generating X-ray contrast image data of the object O by the K absorption edge subtraction method will be described here.

Firstly, a user inputs information, for selecting X-ray imaging by the K absorption edge subtraction method, to the threshold setting part 32 by operating the input circuit 5. Subsequently, the user inputs information, for selecting a contrast agent, to the threshold setting part 32 by operating the input circuit 5. Therefore, the threshold setting part 32 sets energy bands for performing X-ray imaging by the K absorption edge subtraction method with referring to a table, as exemplified in FIG. 10, stored in the threshold storage part 33. Thereby, the energy bands corresponding to the K absorption edge of the contrast agent as exemplified in FIG. 7, FIG. 11, or FIG. 12 are set as counting targets of the number of X-ray photons.

On the other hand, the object O is set on the top plate of the bed 10. Then, a contrast agent is injected into the object O. Subsequently, control signals according to imaging conditions are output from the imaging position control circuit 3B of the control system 3 so that the driving mechanism 9 drives. Thereby, the X-ray exposure part 7 and the X-ray detector 8 are positioned at predetermined positions. Meanwhile, a high voltage is applied to the X-ray tube of the X-ray exposure part 7 from the high voltage generator 3A of the control system 3. Thereby, an X-ray is exposed from the X-ray tube of the X-ray exposure part 7 to an imaging part of the object O.

Then, X-ray photons which have transmitted the object O and the contrast agent are acquired by the X-ray detector 8 as X-ray detection data. Specifically, X-ray detection data sets are acquired in the X-ray detector 8 by counting X-ray photons in the respective energy bands at respective pixel positions.

Subsequently, the X-ray detector 8 outputs the number counting result of X-ray photons by pixel and by energy band to the medical image processing apparatus 15 as a number counting signal of the X-ray photons. Then, generation processing of X-ray contrast image data showing thicknesses of the contrast agent is performed in the subtraction processing part 30 of the medical image processing apparatus 15.

Figure 16:
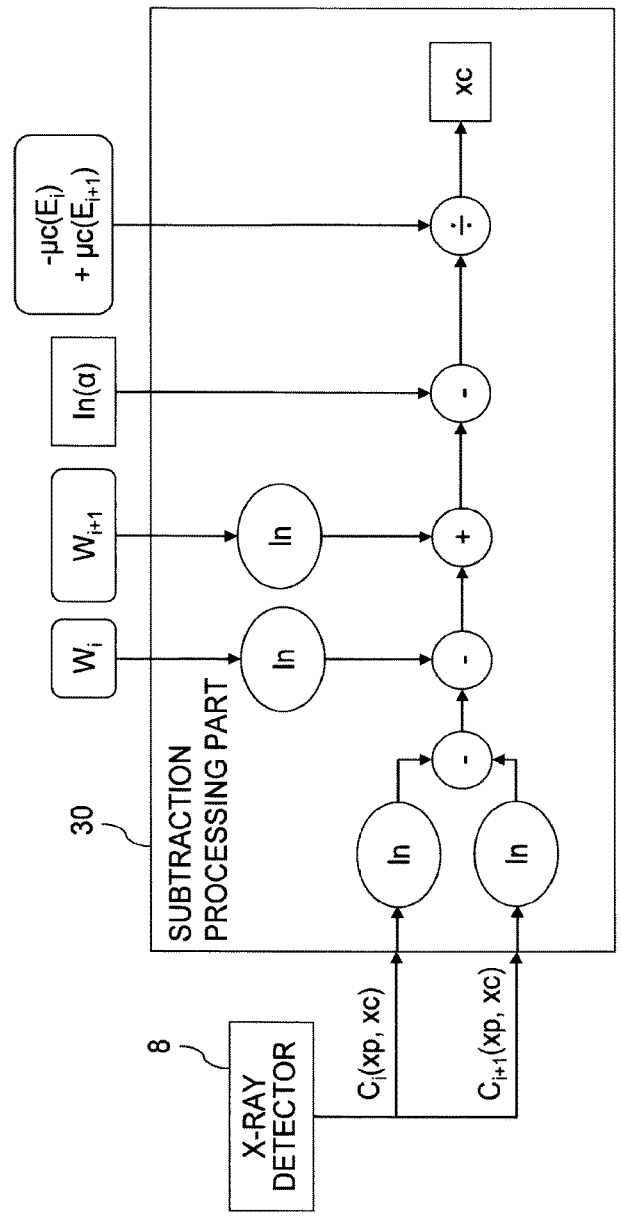
FIG. 16 shows processing performed in the subtraction processing part shown in FIG. 3.

FIG. 16 shows processing performed in the subtraction processing part 30 shown in FIG. 3.

In FIG. 16, each of the rectangular frames indicates numerical values arranged two-dimensionally, and each of the rounded rectangles indicates one numerical value. The number counting signal $C_i(xp, xc)$ of X-ray photons in the i-th energy band and a number counting signal $C_{i+1}(xp, xc)$ of X-ray photons in the (i+1)-th energy band are output from the X-ray detector 8 to the subtraction processing part 30. Then, the subtraction processing part 30 performs the operations shown by expression (18).

Specifically, the subtraction processing part 30 performs logarithmic conversion of the number counting signal $C_i(xp, xc)$ of X-ray photons in the i-th energy band and the number counting signal $C_{i+1}(xp, xc)$ of X-ray photons in the (i+1)-th energy band respectively, and subsequently, performs subtraction processing of the number counting signals $C_i(xp, xc)$ and $C_{i+1}(xp, xc)$ after the logarithmic conversion. Next, the subtraction processing part 30 obtains the width $W_i$ of the i-th energy band and the width $W_{i+1}$ of the (i+1)-th energy band, set as imaging conditions for the X-ray imaging, from the threshold setting part 32. Then, the width $W_i$ of the i-th energy band and the width $W_{i+1}$ of the (i+1)-th energy band are subjected to logarithmic conversion respectively, and subsequently, subtraction processing of the widths $W_i$ and $W_{i+1}$ after the logarithmic conversion is performed.

Next, the subtraction processing part 30 subtracts the result of the subtraction processing of the widths $W_i$ and $W_{i+1}$ of the energy bands after the logarithmic conversion, from the result of the subtraction processing of the number counting signals C (xp, xc) and $C_{i+1}(xp, xc)$ of the X-ray photons after the logarithmic conversion.

Next, the subtraction processing part 30 obtains information, specifying the substance constituting the contrast agent, from the threshold setting part 32. Furthermore, the subtraction processing part 30 obtains conditions for X-ray imaging from the control signal generation part 31, and obtains reference data $\ln\{\alpha(E_i, E_{i+1}, xp, xd)\}$ corresponding to the information, specifying the substance constituting the contrast agent and the obtained conditions, from the calibration data storage part 35. Then, the subtraction processing part 30 performs subtraction processing by the reference data $\ln\{\alpha(E_i, E_{i+1}, xp, xd)\}$.

Next, the subtraction processing part 30 obtains the X-ray absorption coefficients $\mu c(E_i)$ and $\mu c(E_{i+1})$ of the contrast agent, corresponding to the i-th energy band and the (i+1)-th energy band respectively, from the absorption coefficient storage part 36, based on the information specifying the substance constituting the contrast agent. Then, the subtraction processing part 30 performs division processing using a value derived by subtracting the X-ray absorption coefficient $\mu c(E_i)$ of the contrast agent, corresponding to the i-th energy band, from the X-ray absorption coefficient $\mu c(E_{i+1})$ of the contrast agent corresponding to the (i+1)-th energy band.

As a result, X-ray contrast image data showing the thicknesses xc of the contrast agent are generated. The X-ray contrast image data can be superimposed and displayed or displayed in parallel with X-ray image data showing the structure of the object O. In that case, X-ray image data showing information with regard to the object O are generated in the X-ray image generation part 34 based on number counting results of X-ray photons in all the energy bands.

When the X-ray image data showing the structure of the object O and the X-ray contrast image data are displayed in parallel, the X-ray image data showing the structure of the object O and the X-ray contrast image data are displayed in parallel on the display 6 through the display processing part 41.

Meanwhile, when the X-ray image data showing the structure of the object O and the X-ray contrast image data are superimposed and displayed with each other, composite image data combined by weighting addition processing in the image composition part 38 are displayed on the display 6 through the display processing part 41. Note that, filter processing for reducing noise of the X-ray contrast image data is performed in the filter processing part 40 while compression processing of a dynamic range of the X-ray image data showing the structure of the object O is performed in the compression processing part 39, before the weighting addition processing.

That is, the X-ray diagnostic apparatus 1 as described above is configured to determine practical and appropriate energy bands of X-ray photons according to the K absorption edge of an X-ray absorber of interest, such as a contrast agent, and to perform X-ray imaging by the K absorption edge subtraction method using the photon counting type X-ray detector 8.

Effects

Therefore, the X-ray diagnostic apparatus 1 allows performing X-ray imaging by the K absorption edge subtraction method, without using a special X-ray source which exposes a monochromatic X-ray. In other words, X-ray imaging by the K absorption edge subtraction method can be performed using an X-ray having an energy spectrum distributed continuously.

In particular, the appropriate number of energy bands of X-ray photons, appropriate widths of the energy bands, and appropriate levels of the energy bands to be counting targets in the X-ray detector 8 can be respectively set according to the K absorption edge of an X-ray absorber of interest, such as a contrast agent. Therefore, the number of the energy bands where the X-ray detector 8 should count the numbers of X-ray photons can be minimized appropriately.

When the number of the energy bands to be counting targets of X-ray photons is increased, the number of the comparators 24 which should be included in the X-ray detector 8 also increases. Therefore, the large number of energy bands more than necessary leads to an increase in a circuit size of the X-ray detector 8, which may cause unreality. Conversely, when the number of the energy bands is made extremely small in order to make the circuit size of the X-ray detector 8 practical, the energy bands may not be set appropriately according to the K absorption edge.

By contrast, the X-ray diagnostic apparatus 1 allows appropriate setting of the number of energy bands, widths of the energy bands, and levels of the energy bands according to the K absorption edge of an X-ray absorber of interest. On the other hand, energy bands can be also appropriately set for usual X-ray imaging which is not performed by the K absorption edge subtraction method. Therefore, X-ray imaging by the K absorption edge subtraction method and usual X-ray imaging can be performed using the photon counting type of X-ray detector 8 having a practical circuit size.

In addition, energy bands of X-ray photons can be set according to a K absorption edge of not only a contrast agent but also a substance constituting a medical agent or a device, such as a guide wire, a catheter, or a stent. Specifically, the threshold setting part 32 can set two X-ray energy bands depending on a K absorption edge of at least one of a contrast agent, a medical agent, and a device. Therefore, X-ray image data in which an X-ray absorber of interest has been depicted so as to be satisfactorily visually recognized can be generated.

For example, when iodine is depicted, the visibility of blood vessels or perfusion can be improved. Alternatively, when barium is depicted, the visibility of the inner wall of a digestive tract can be improved. Furthermore, the visibility of a desired substance or object, such as a medical agent, a stent, or a catheter, can also be improved. As described above, the visibility can be improved using a K absorption edge of not only limited to iodine as in the past but also a variety of targets.

In addition, since the X-ray diagnostic apparatus 1 exposes an X-ray having a continuous energy spectrum, an X-ray having energies larger and smaller than the K absorption edge is simultaneously exposed to the object O. Therefore, influence of a motion of the object O, which has been a problem in the conventional method of intermittently exposing two monochromatic X-rays having different energies, can be avoided.

Furthermore, the X-ray diagnostic apparatus 1 allows generating X-ray image data using not only number counting results of X-ray photons counted in energy bands lower and higher than the K absorption edge, but also number counting results of X-ray photons counted in other energy bands. That is, X-ray detection data which are not used for data processing for the K absorption edge subtraction method can be used for imaging. Therefore, unnecessary radiation exposure of the object O can be reduced and data can be effectively utilized.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

In the above-mentioned example, description has been made for the case where a table showing appropriate widths $W_i$ and $W_{i+1}$ of energy bands corresponding to X-ray absorbers and imaging conditions, as exemplified in FIG. 10, is stored in the threshold storage part 33 so that the threshold setting part 32 can specify threshold voltages, which should be applied to the respective comparators 24, based on the corresponding widths $W_i$ and $W_{i+1}$ of energy bands obtained from the threshold storage part 33. As another example, threshold voltages themselves which should be applied to the respective comparators 24 may be stored in the threshold storage part 33. In that case, the threshold setting part 32 obtains corresponding threshold voltages, which should be applied to the respective comparators 24, from the threshold storage part 33, based on information specifying an X-ray absorber, obtained from the input circuit 5, and imaging conditions to determine radiation quality of X-ray, obtained from the control signal generation part 31.

FIG. 17 shows an example of table showing threshold voltages to be stored in the threshold storage part 33 shown in FIG. 3.

As shown in FIG. 17, the threshold voltages TH1, TH2, and TH3 which should be applied to the comparators 24 can be stored in the threshold storage part 33 as a table for every imaging purpose, every X-ray absorber to be used, every tube voltage, and every beam filter to be used. In the example shown in FIG. 17, the widths $W_1$ and $W_2$ of energy bands corresponding to the threshold voltages TH1, TH2, and TH3 have been also related to the imaging purposes, the X-ray absorbers to be used, the tube voltages, and the beam filters to be used.

When the above-mentioned table is stored in the threshold storage part 33, the threshold setting part 32 can set the threshold voltages TH1, TH2, and TH3, corresponding to information input from the input circuit 5, only by selecting the threshold voltages TH1, TH2, and TH3 from the threshold storage part 33. Then, the threshold voltages TH1, TH2, and TH3 selected by the threshold setting part 32 can be applied to the comparators 24.

As a matter of course, each threshold voltage for determining a boundary of energy bands other than the K absorption edge can also be stored as a table in the threshold storage part 33. Then, the threshold voltages TH1, TH2, TH3, . . . , THm for performing not only X-ray imaging by the K absorption edge subtraction method but also usual X-ray imaging can be specified with referring to a table stored in the threshold storage part 33.

What is claimed is:

1. An X-ray diagnostic apparatus, comprising:
   an X-ray tube configured to expose an X-ray toward an object;
   an X-ray detector configured to acquire two X-ray detection data sets by counting X-ray photons in at least two X-ray energy bands depending on a K absorption edge of an X-ray absorber taken into the object, the X-ray photons having transmitted to the object; and
   processing circuitry configured to:
      input information to specify the X-ray absorber;
      set the at least two X-ray energy bands based on the input information to specify the X-ray absorber; and
      generate at least one frame of X-ray image data by data processing including subtraction processing of the two X-ray detection data sets, the X-ray absorber having been depicted in the at least one frame of X-ray image data,
   wherein the processing circuitry is further configured to set a boundary between the at least two X-ray energy bands to be higher than an energy at the K absorption edge by a predetermined amount.

2. An X-ray diagnostic apparatus of claim 1, wherein the processing circuitry is further configured to set plural sets of two X-ray energy bands based on information to specify X-ray absorbers, the plural sets of two X-ray energy bands depending on K absorption edges of the X-ray absorbers, respectively.

3. An X-ray diagnostic apparatus of claim 1, further comprising:
   a storage circuit configured to store pieces of information related with X-ray absorbers, respectively, the pieces of information being used to determine sets of two X-ray energy bands depending on K absorption edges of the X-ray absorbers, respectively,
   wherein the processing circuitry is further configured to obtain a piece of information from the storage circuit, the piece of information being used to determine two X-ray energy bands corresponding to the piece of information to specify the X-ray absorber.

4. An X-ray diagnostic apparatus of claim 3,
   wherein the storage circuit is further configured to store the pieces of information for determining the sets of two X-ray energy bands, the pieces of information being further related with at least one of X-ray tube voltages, each possibly applied to the X-ray tube, and pieces of information identifying beam filters, each possibly placed in an output side of the X-ray tube; and
the processing circuitry is further configured to set the at least two X-ray energy bands based on at least one of an X-ray tube voltage and a beam filter corresponding to an exposure condition of an X-ray exposed from the X-ray tube.

5. An X-ray diagnostic apparatus of claim 1, wherein the processing circuitry is further configured to:
set at least three X-ray energy bands including the at least two X-ray energy bands and at least one X-ray energy band other than the at least two X-ray energy bands; and
generate X-ray image data having a contrast which does not correspond to the K absorption edge, based on X-ray detection data corresponding to at least one of the at least three X-ray energy bands.

6. An X-ray diagnostic apparatus of claim 5, wherein the processing circuitry is further configured to set at least one of first X-ray energy bands in which each X-ray energy band of the first X-ray energy bands is higher than any of the at least two X-ray energy bands and second X-ray energy bands in which each X-ray energy band of the second X-ray energy bands is lower than any of the at least two X-ray energy bands, the first X-ray energy bands and the second X-ray energy bands being included in the at least one X-ray energy band that is other than the at least two X-ray energy bands, the first X-ray energy bands having a first equal bandwidth, and the second X-ray energy bands having a second equal bandwidth.

7. An X-ray diagnostic apparatus of claim 5, wherein the processing circuitry is further configured to combine the X-ray image data, in which the X-ray absorber has been depicted, with the X-ray image data having the contrast which does not correspond to the K absorption edge.

8. An X-ray diagnostic apparatus of claim 1, wherein the processing circuitry is further configured to input at least one of an examination item and information to specify a contrast agent, as the information to specify the X-ray absorber.

9. An X-ray diagnostic apparatus of claim 1, wherein the processing circuitry is further configured to:
set two sets of at least two X-ray energy bands based on information to specify two X-ray absorbers, the two sets depending on K absorption edges of the two X-ray absorbers respectively; and
generate four frames of X-ray image data corresponding to at least the two sets of the two X-ray energy bands.

10. An X-ray diagnostic method, comprising:
inputting information to specify an X-ray absorber taken into an object;
setting at least two X-ray energy bands based on the input information to specify the X-ray absorber, the at least two X-ray energy bands depending on a K absorption edge of the X-ray absorber;
exposing an X-ray toward the object;
acquiring two X-ray detection data sets by counting X-ray photons in the at least two X-ray energy bands, the X-ray photons having transmitted to the object; and
generating at least one frame of X-ray image data by data processing including subtraction processing of the two X-ray detection data sets, the X-ray absorber having been depicted in the at least one frame of X-ray image data,
wherein the setting step further includes setting a boundary between the at least two X-ray energy bands to be higher than an energy at the K absorption edge by a predetermined amount.

* * * * *